United States Patent [19]
Williams et al.

[11] Patent Number: 5,089,406
[45] Date of Patent: Feb. 18, 1992

[54] METHOD OF PRODUCING A GENE CASSETTE CODING FOR POLYPEPTIDES WITH REPEATING AMINO ACID SEQUENCES

[75] Inventors: Jon I. Williams, Montclair; Anthony J. Salerno, Millington; Ina Goldberg, Gillette; William T. McAllister, Metuchen, all of N.J.

[73] Assignee: Allied-Signal Inc., Morristownship, Morris County, N.J.

[21] Appl. No.: 476,112

[22] Filed: Jan. 29, 1990

Related U.S. Application Data

[63] Continuation of Ser. No. 1,292, Jan. 7, 1987, abandoned.

[51] Int. Cl.$^5$ .............. C12N 15/00; C12N 15/10; C12P 21/02; C07K 13/00
[52] U.S. Cl. .................. 435/172.3; 435/69.1
[58] Field of Search ............ 435/172.3, 69.1, 320.1, 435/172.1, 170; 935/10

[56] References Cited

U.S. PATENT DOCUMENTS

| | | | |
|---|---|---|---|
| 3,476,624 | 11/1969 | Hogya et al. | 156/659.1 |
| 4,132,746 | 1/1979 | Urry et al. | 525/432 |
| 4,237,224 | 12/1980 | Cohen et al. | 435/69.1 |
| 4,495,287 | 1/1985 | Uhlin et al. | 435/231 |
| 4,530,901 | 7/1985 | Weissman | 435/69.51 |
| 4,551,433 | 11/1985 | DeBoer | 435/252.33 |
| 4,563,424 | 1/1986 | Riggs | 435/69.4 |
| 4,578,355 | 3/1986 | Rosenberg | 435/320.1 |

FOREIGN PATENT DOCUMENTS

| | | |
|---|---|---|
| 83/13547 | 10/1983 | European Pat. Off. |
| 0141484A2 | 6/1984 | European Pat. Off. |
| 0131843A1 | 7/1984 | European Pat. Off. |
| 0152736A2 | 1/1985 | European Pat. Off. |
| 0136090A2 | 4/1985 | European Pat. Off. |
| 0163406A1 | 4/1985 | European Pat. Off. |
| 0154576A1 | 5/1985 | European Pat. Off. |
| 0161937A2 | 11/1985 | European Pat. Off. |
| 2162190A | 1/1986 | European Pat. Off. |
| 86/00911 | 2/1986 | European Pat. Off. |
| 86/01210 | 2/1986 | European Pat. Off. |
| 2162190 | 1/1986 | United Kingdom ............ 435/69.1 |

OTHER PUBLICATIONS

Doel et al, Nucleic Acids Res. 8: 4575-4592 (1980).
Kempe et al, Gene 39: 239-245 (1985).
Willson et al, Gene Anal. Techn. 2: 77-82 (1985).
Wells et al, Gene 34: 315-323 (1985).
Hartley et al, Gene 13: 347-353 (1981).
Shen, S-H. 1984, *Proc. Nat. Acad. Sci. USA*, vol. 81, pp. 4627-4631.
Kempe, T. et al., 1985, *Gene*, vol. 39, pp. 239-245.
D. Hanahan, *Studies on Transformation of Escherichia coli with Plasmids*, J. Mol Biol. (1983) 166,557-580.
T. A. Willson et al. *A Simple Method for Constructing Directly Repeated Multermic DNA Segments* 1985 Elsevier Sc. Pub, 77-82.
J. H. Kelly et al, *Hybrid Genes: Molecular Approaches to Tissue Specific Gene Regulation* 273-296.
K. Nordstrom, Control of Replication of Bacterial Plasmids: *Genetics* . . . Plasmid 12, 71-90 (1984).
J. A. Lautenberger et al. *High-level expression in Escherichia coli of the carboxy-terminal* . . . Genes 23 (1983) 75-84.
C. A. Caulcott et al. *Temperature-induced synthesis of recombin proteins* 142-145 Tibtech-Jun. 1986.
P. Stanssens, et al. *Alterations upstream form the Shine--Dalgar region and their effect* . . . Gene 36 (1985) 211-223.

(List continued on next page.)

*Primary Examiner*—Richard A. Schwartz
*Assistant Examiner*—M. E. Mosher
*Attorney, Agent, or Firm*—Darryl L. Webster; Richard C. Stewart

[57] ABSTRACT

This invention relates to processes for the microbial production of peptide oligomers, to polypeptide products resulting from application of any of these processes, and to microbes for use in such production. Another aspect of this invention relates to processes for genetically engineering such microbes and to plasmid vectors for use in such engineering.

18 Claims, 1 Drawing Sheet

OTHER PUBLICATIONS

A. M. Chakrabarty, Ph.D. *Genetic Engineering/Ch 4 Plasmid Clonin Vectors* 83–111.

R. Wu et al. *Genetic Engineering Technology–An Overview and Some Recent Advances* 3–21.

E. Remaut et al. *Plasmid vectors for high-efficiency expression controlled* . . . Gene 15 (1981) 81–93.

E. Amann et al. *ATG vectors' for regulated high-level expression of cloned genes* . . . Gene 40 (1985) 183–190.

N. Lee et al. *Cloning with tandem gene systems for high level gene expression* vol. 12/ No. 17 6797–6812.

R. N. Rao *Construction and properties of plasmid PKC30* Gene 31 (1984) 247–250.

B. J. Pierson et al. *Electrochemical survey of selected cations* . . . FJ SR1-TR-82-004 Sep. 1982.

A. Seth et al. *High-level expression vectors to synthesize .* . . Gene 42 (1986) 49–57.

K. Bachman et al. *Maximizing Gene Expression on a Plasmid Using Recombination in Vitro* Cell vol. 13 65–71 Jan. 1978.

J. H. Miller Experiments in Molecular Genetics *Generalized Transduction; Use of P1* . . . (Experiment 28) 201–205.

R. J. Zabursky et al. *Rapid and Easy Sequencing of Large Linear Double-Stranded* . . . 1985 Gene Anal Techn 2:89–94.

E. Lazarides *Intermediate filaments as mechanical integrators of cellular space* Nature, vol. 283, Jan. 17, 1980.

A. D. McLachlan *Tests for Comparing Related Amino-Acid Sequence Cytochrome c* . . . J. Mol Biol. (1971) 61,409–424.

E. Amann, J. Brosius & M. Ptashne, *Vectors bearing a hybrid trp-lac* . . . Gene 25 (1983) 167–178.

L. Guarente, *Use of Gene Fus-ions to Study Biological Problems,* vol. 6, Genetic Engineering 233–248.

J. L. Hartley et al. *Cloning multiple copies of a DNA segment* Gene 13 (1981) 347–353.

T. S. Papas et al. *Novel Plasmid PJL6* PAT-APPL-6-511 108 Wa/DO Jul. 6, 1983.

H. A. DeBoer et al. *The tac promoter: A functional hybrid derived from the trp* . . . Proc Nat Sci, vol. 80, 21–25 Jan. 83.

A. Sugino et al. *Interaction of Bacteriophage T4 RNA and DNA* . . . Journal of Biol. Chem., vol. 252.

S. B. Needleman et al. *A General Method Applicable to the Search for Similarities* . . . J. Mol. Biol (1970) 48 443–453.

H. A. Deboer, et al. *Construction of a Tandem trp–lac Promoter and a Hybrid trp–lac promoter* . . . 462–480 Promoters (Structure and Function).

A. M. Maxam & W. Gilbert, *Sequencing End-Labeled DNA with Base-Specific Chemical Cleavages* Methods in Enzymology, vol. 65, 499–560.

G. D. Stormo, et al., *Characterization of translational initiation sites in E. coli* Nucleic Acids Research, vol. 110, No. 9 (1982) 2971–2996.

B. E. Uhlin et al., *Plasmids with Temperature-Dependent Copy Number for Amplification of Clones Genes and Their Products* Gene 6 (1979) 91–106.

M. H. Caruthers et al., *New Methods for Synthesizing Deoxyoligonucleotides* Genetic Engineering, vol. 4, 1–17.

M. Baringa et al., *Methods for the Transfer of DNA, RNA and Protein to Nitrocellulose and Diazotized Paper Solid Supports* Schleicher & Schuell.

J. A. Lautenberger et al., *High-level Expression in Excherichia coli of the carboxy-terminal sequences of the avian* . . . Gene 23 (1983) 75–84.

E. Y. Chen et al., Laboratory Methods *Supercoil Sequencing: A Fast and Simple Method for Sequencing Plasmid DNA* DNA, vol. 4, No. 2 (1985) pp. 165–170.

Tomas, Kempe, Steven B. H. Kent et al., *Multiple-copy genes: production and modification of monomeric peptides* . . . Gene 39 (1985) 239–245.

A. Rattray et al., Control of Bacteriophase Lambda cII Activity by . . . Journal of Bacteriology, Jul. 1984, 238–242, vol. 159.

A. Shatzman et al., *Use of Phage (Gamma) Regulatory Signals to Obtain Efficiency Expression of Genes in Escherichia coli* Experimental Manipulation of Gene Exp., Chap. 1, pp. 1–14.

Maniatas, *Cloning Double-Stranded cDNA by Sequential Addition of Linkers,* pp. 243–246.

Maniatis, *Transformation of Exherichia coli by Plasmid DNA* 249–255.

Maniatis, *Molecular Cloning, A Laboratory Manual* pp. 113–114.

Maniatis, *Electrophoresis of RNA through Gels Containing Formaldehyde* pp. 202–203.

E. Amann & J. Brosius, *ATG vectors' for regulated high-level expression of cloned genes in Escherichia coli* Gene 40 (1985) 183–190.

N. Lee, J. Cozzitorto, N. Wainwright & D. Testa, *Cloning with tandem gene systems for high level gene expression* vol. 12/No. 17, 6797–6812.

M. T. Doel et al., *The expression in E coli of synthetic repeating polymeric genes coding* . . . 4575–4592, vol. 8, No. 20.

B. H. Pheiffer et al. *Polymer-stimulated litigation: enhanced blunt- or cohesive—end* . . . Nucl. Acid, vol. 11, No. 22, 1983, 7853–7871.

D. Eisenberg et al. *The hydriogibuc moment detects* . . . Proc Natl Acad Sci, vol. 81, 140–144, Jan. 1984, 140–144.

L-H Guo et al. *New rapid methods for DNA sequencing based on* . . . Nucl. Acid Research, vol. 10, No. 6, 1982, 2065–2084.

S. L. Beaucage et al. *Deosynucleoside phosphoramidites–A new class of key intermediates* . . . Tetrahedron ltrs. vol. 22, No. 20, 1859, 1862.

FIG. 1

Physical Map of the Expression Vector pAV1

METHOD OF PRODUCING A GENE CASSETTE CODING FOR POLYPEPTIDES WITH REPEATING AMINO ACID SEQUENCES

This application is a continuation of application Ser. No. 001,292, filed Jan. 7, 1987, now abandoned.

FIELD OF THE INVENTION

This invention relates to processes for the microbial production of peptide oligomers, to polypeptide products resulting from application of any of these processes, and to microbes for use in such production. Another aspect of this invention relates to processes for genetically engineering such microbes and to plasmid vectors for use in such engineering.

PRIOR ART

Procedures for genetically engineering microbes are known. Illustrative of certain aspects of these procedures relevant to this application are those described in G. D. Stormo, T. D. Scheider and L. M. Gold, *Nucleic Acids Research* 10, 2971-2996 (1982); A. Shatzman, Y. S. Ho and M. Rosenberg in *Experimental Manipulation of Gene Expression*, pp. 1-14. M. Inouye, ed. (Academic Press, 1983); A. Rattray, S. Altuvia, G Mahagna, A. B. Oppenheim and M. Gottesman, Journal of Bacteriology 159, 238-242 (1984).

Modern biochemical advances in genetic technology have led to the introduction of new techniques for transferring genes between soecies. Many of these techniques are based on the use of plasmid vectors with microorganisms as hosts. These vectors allow establishment and expression of foreign genes in microorganisms such as bacteria under controllable conditions. See J. G. Sutcliffe and F. M. Ausubel in *Genetic Engineering*, pp. 83-111. A. M. Chakrabarty, ed. (CRC Press, 1978) and R. Wu, L.-H. Guo and R.C. Scarpella in *Genetic Engineering Techniques*, pp. 3-21. P. C. Huang, T.T. Kuo and R. Wu, eds. (Academic Press, 1982). A large number of plasmids are now available that allow cloning of either genes with their naturally associated regulatory DNA sequences or genes which function under the control of regulatory DNA sequences inherent to the parent plasmid. Many of these plasmids have been applied to the isolation, characterization and expression of many genes, gene fragments or gene promoter sequences. Most of the genes which have been cloned and expressed from plasmid vectors in bacteria such as the gram-negative bacterium *Escherichia coli* code for proteins which are enzymes or which have a physiologic function (e.g., hormones, blood factors, cell growth factors, etc.). Relatively few genes or gene fragments have been cloned that code for all or part of a structural protein such as components of the extracellular matrix in multicellular higher organisms; these proteins include the collagen family, elastin, fibronectin, laminin and other fibrous proteins. Other structural proteins with interesting physical or chemical properties include the protein or glycoprotein elements of thick, intermediate or thin filaments in higher organisms, the annelid or arthropod silks, bacterial flagellin, resilin, eucaryotic egg shell proteins, insect cuticle proteins and architectural proteins involved with eucaryotic developmental processes such as tissue organization. Very few of these cloned genes have been expressed and their protein products isolated, purified and/or biochemically analyzed following their expression in a heterologous bacterial host.

Researchers in recombinant DNA technology using the bacterial host *E. coli* who have been or who are interested in optimizing foreign gene expression from plasmid vectors have utilized various strategies for increasing protein production from the foreign genes. These strategies include use of runaway replication of the plasmid vector, thermal or chemical induction of the promoter DNA sequence controlling expression of the foreign gene, or use of highly active promoter sequences such as the lac, tro or lpo promoters endogeneous to *E. coli*or natural or synthetic mutant forms thereof. For illustrative examples of such efforts, see B. Uhlin, S. Molin, P. Gustafsson and K. Nordstrom, *Gene* 6, 91-106 (1979); K. Backman and M. Ptashne, *Cell* 13, 65-71 (1978); K. Nordstrom, S. Molin and J. Light, *Plasmid* 12, 71-90 (1984); and P. Stanssens, E. Remaut and W. Fiers, *Gene* 36, 211-223 (1985). Hybrid promoters which advantageously use a $-35$ consensus sequence and a 5' flanking region from one promoter and a portion of a promoter/operator sequence including a $-10$ region sequence and a Shine-Delgarno sequence from a second natural or synthetic promoter/operator DNA sequence have proven particularly useful for high level expression of foreign genes in *E. coli*. See literature, in the case of hybrid tro-lac promoters, such as H. A. DeBoer, L. J. Comstock and M. Vasser, *Proc. Natl. Acad. Sci.* 80, 21-25 (1983); E. Amann, J. Brosius and M. Ptashne, *Gene* 25, 167-178 (1983); U.S. Pat. 4,551,433, issued Nov. 5, 1985 to H. A. DeBoer; and European patent application 0136090 (filed Aug. 24, 1985) by R. Arentzen and S. R. Petteway, Jr. Plasmid vectors utilizing the controlling elements of the bacteriophage lambda PL promoter in concert with additional elements such as temperature-sensitive expression of the cI repressor protein governing activity from the $P_L$ promoter and the nutL locus for antitermination activity mediated by the bacteriophage N protein have also provided high levels of foreign gene expression in *E. coli* and proved comparatively to be as strong or stronger than other strong promoters such as the lacUV5 promoter in *E. coli*. See especially E Remaut, P. Stanssens and W. Fiers, *Gene* 15, 81-93 (1981); U.S. Pat. No. 4,578,355, issued Mar. 25, 1986 to M. Rosenberg; J. A. Lautenberger, D. Court and T. S. Papas, *Gene* 23, 75-84 (1983); and European patent application 0131843 (field Mar. 7, 1984) by H. Aviv, M. Gorecki, A. Levanon, A. Oppenheim, T. Vogel, E. Zeelon, and M. Zeevi; and C. A. Caulcott and M. Rhodes, *Trends in Biotechnology* 4, 142-146 (1986). Most of these publications describe cloning of foreign genes in phase with an initiation codon ATG and production of a fusion protein under the control of the lambda PLOL promoter operator system, N protein-nutL interaction and the lambda cII gene ribosomal binding site. The product fusion protein then includes some portion of the amino terminus peptide sequence from the bacteriophage lambda cII protein.

Applicants are aware that the Department of Health and Human Services, U.S.A., under the names of T. S. Papas and J. A. Lautenberger filed a U.S. Pat. application under Ser. No. 6-511,108 on July 6, 1983 covering the plasmid pJL6. Portions of this application have been obtained from the National Technical Information Service, U.S. Department of Commerce. However, the claims are not available and are maintained in confidence. The available portions of the application have been reviewed. The construction of oJL6 is described and its use as a cloning and expression vector for heterologous genes is discussed with relevant examples drawn exclusively from molecular cloning experiments with oncogenes. No mention is made in the available application portions of the use of recombination deficient bacterial hosts, the cloning of synthetic genes or genes coding for structural proteins, or cloning into restriction enzyme recognition sites in pJL6 other than the ClaI site or the ClaI-BamHI site pair. All heterologous genes therefore cloned in oJL6 will necessarily produce fusion protein products whereby the foreign gene product cannot be prepared free of amino acid residues on the amino terminus which derive from the lambda cII gene.

A. Seth, P. Laois, G. F. Van de Woude and T. S. Papas in *Gene* 42, 49-57 1986) describe modification of the expression vector oJL6 to yield a class of plasmid vectors which contain in 5' to 3' order: the lambda bacteriophage PLOL promoter/operator sequence, an N gene-cro gene fusion polypeptide, the N gene utilization site (nutL), a ribosomal binding site from the lambda cII gene and a restriction enzyme recognition site which is adjacent to the initiation codon ATG and which allows insertion of foreign genes in phase with the initiation codon so as to code for a protein product with at most one extraneous amino acid residue. The plasmids constructed by A. Seth et al. were specifically designed to be cleaved by an appropriate restriction enzyme and treated with S1 nuclease and also have an NdeI restriction enzyme recognition site which includes the initiation codon ATG as well as a second NdeI restriction site downstream of the unique HpaI, BamHI or KpnI restriction sites described as useful for cloning foreign genes. This article makes no mention of cloning synthetic genes or production of structural proteins for other than the propose of biochemical research studies. Any advantages of the use of *E. coli* recombination deficient bacterial hosts for these plasmids is also not disclosed nor discussed by these authors.

H. Aviv et al. (pp. cit.) claim as a composition of matter vectors which include in 5' to 3' order: a DNA sequence which contains the promoter and operator $P_LO_L$ from bacteriophage lambda, the N gene utilization site for binding antiterminator N protein produced by the host cell, a DNA sequence which contains a ribosomal binding site for rendering the mRNA of the desired gene capable of binding to ribosomes within the host cell, an ATG initiation codon or a DNA sequence which is converted into an ATG initiation codon upon insertion of the desired foreign gene into the vector, and a restriction enzyme recognition site for inserting the desired foreign gene into the vector in phase with the ATG initiation codon. This type of vector does not necessarily suffer from potential disadvantages of producing fusion proteins with unwanted amino acid residues at the amino terminus which cannot be conveniently removed. No mention is made in this patent application of cloning of synthetic genes or of genes with repeating amino acid sequences, of cloning of structural proteins or proteins with interesting physical properties, or of the utility or preferred use of *E. coli* recombination-deficient bacterial hosts for gene expression from the claimed plasmid vectors.

Gene fusions and hybrid genes have been known in the art of molecular genetics for a number of years. For example, see L. Guarente in *Genetic Engineering, Principles and Methods - Volume* 6, pp. 233-248 (J. K. Setlow and A. Hollaender, eds.; Plenum Press, 1984) and J. H. Kelly and G. J. Darlington, *Annual Reviews of Genetics* 19, 273-296 (1985) for reviews. Also see world patent applications WO 83/03547 (U.S.A. priority date Apr. 14, 1982) by J. L. Bittle and R. A. Lerner, WO 85/02611 (filed Dec. 12, 1984) by R. A. Houghten for the Scripps Clinic and Research Foundation and WP 86/01210 (filed August 1985) by D. A. Carson, G. Rhodes and R. Houghten for the Scripps Clinic and Research Foundation, and European patent applications EPA 0141484 (GB priority date June 10, 1983) by C. Weissman and H. Weber for Biogen N.V., EPA 0152736 (GB priority date Nov. 1, 1984) by H. Ferres, R.A.G. Smith and A. J. Garman for Beecham Group P.L.C.1, and EPA 0161937 (GB priority date May 16, 1984) by K. Nagai and H. C. Thogersen for Celltech Ltd. All of these patent applications describe the production of fusion or hybrid proteins for a variety of pharmacological agents, enzyme conjugates and diagnostic methods and kits. None of these applications, however, refers to the production of proteins preferred for their physical or structural properties, the production of peptides or proteins from synthetic genes or discusses a requirement to produce recombinant products in recombination-deficient bacterial hosts. Some of these applications claim peptide or protein products with internally repeating amino acid sequences, including oligomers of a native protein, but without exception these products as discussed in the relevant applications are pharmacologically or antigenically active compounds.

As another aspect of the art of molecular cloning pertinent to the invention described herein, it should be noted that several research groups have successfully cloned synthetic genes. Very few of these cloning efforts have focused on peptide or protein products with internally repeating amino acid sequences. The cloning of a synthetic gene coding for a polymeric form of an oligopeptide, specifically the dipeptide L-aspartyl-L-phenylalanine, is disclosed in M.T. Doel et al., *Nucleic Acids Research* 8, 4575-4592 (1980). A requirement therein for the use of a recombination-deficient host is recognized by the employment of *E. coli* strain HB101 (genotype recA13) which is widely used in the art of molecular cloning. However, these researchers only describe a process for producing polymeric forms of short oligopeptide which could be subsequently broken down chemically or enzymatically into short oligopeptides and do not address any potential advantages to production and use of the polymeric peptides directly. The method described in this reference also is limited to those synthetic genes which can be constructed by annealing two completely complementary oligodeoxynucleotides so as to create DNA hybrids with staggered ends that can further anneal into large oligomeric synthetic DNA sequences. There is no disclosure in this reference of any method to further oligomerize the synthetic gene products into even larger synthetic genes.

Other literature in the art of molecular cloning and peptide or protein expression has dealt with the problem of DNA segment oligomerization. Strategies have been presented in several of these references for specifically and efficiently linking equivalent DNA segments into long DNA sequences which code in an uninterrupted fashion for a large peptide or protein product with internally repeating sequence. See J. L. Hartley and T. J. Gregori, *Gene* 13, 347-353 (1981); T. A. Willson et al., *Gene Analytical Techniques* 2, 77–82 (1985); and T. Kemoe et al. *Gene* 39, 239–245 (1985). In contrast to the current invention, none of these references discloses production of synthetic genes coding for repeating amino acid sequences which are of essential value in the polymerized state or discloses the preferred use of recombination-deficient bacterial hosts for plasmid expression vectors bearing synthetic genes. The examples and discussion in these articles bear only on aggregates or oligomers of protein or peptide products which are pharmacologically active or have an undisclosed activity.

S. Petty-Saphon and J. A. Light have claimed in U.K. patent application GB 2162190 (filed July 8, 1985) a method of producing polypeptide products which are components of silk including those wherein the silk protein comprises sets of the sequence (Gly-Ala-Gly-Ala-Gly-Ser). However this application is not enabling since no examples are given, appropriate plasmid expression vectors and suitable bacterial hosts or other host microorganisms or plant or animal cell hosts are not identified and a method of producing or isolating a natural or synthetic gene encompassing the aforementioned sets of the sequence (Gly-Ala-Gly-Ala-Gly-Ser) is not described.

SUMMARY OF THE INVENTION

One aspect of this invention relates to a method of preparing double-stranded DNA fragments which code totally for a repeating amino acid sequence for insertion into plasmid vectors, which process comprises the steps of:

(a) annealing a mixture comprising at least two complementary phosphorylated DNA oligodeoxynucleotides which partially overlap upon base pairing by heating said mixture and thereafter slowly cooling said mixture to allow formation of stable base pairs between complementary sequences oriented antiparallel with respect to their 5' to 3' polarity;

(b) treating said mixture of annealed DNA oligodeoxynucleotides with a ligase enzyme to covalently link adjacent oligodeoxynucleotides with the same 5' to 3' polarity into longer DNA segments;

(c) enzymatically attaching duplex oligodeoxynucleotide linker DNAs to said covalently linked DNA segments to provide double-stranded DNA fragments having linkers attached to the ends thereof, said DNA linkers including at least one restriction enzyme recognition site which is unique to the linkers which is not found within the repeating oligodeoxynucleotide sequences of said double-stranded DNA fragments and which occurs not more than once within the sequences of some plasmid vector, said linker DNAs having nonequivalent single-stranded chain ends, and said linkers also adapted to maintain the genetic code reading frame and to maintain the repeating amino acid sequence of one or more of said DNA segments when attached enzymatically in tandem to said plasmid vector.

Another aspect of this invention relates to double-stranded DNA sequences prepared by the process of this invention and;

A preferred embodiment of the process of this invention further comprises cleaving said linkers with a restriction enzyme so as to eliminate multimeric forms of linker ends on said DNA fragments or oligomerized forms of said DNA fragments.

In another preferred embodiment of the process of this invention the covalently linked base paired complementary DNA sequences are further treated with a DNA polymerase prior to attachment of linkers to totally or partially remove nicks or gaps in the base-paired synthetic DNA sequences. In yet another preferred embodiment of the process of this invention steps (b) and (c) are conducted simultaneously. Still another preferred embodiment of the process of this invention further comprises cooling the oligodeoxynucleotide mixture in step (a) of the present invention at a rate and to an extent sufficient to allow formation of hybridized oligodeoxynucleotide strands base paired to provide the maximum amount of overlap between said oligodeoxynucleotides.

In still another preferred embodiment the process of this invention further comprises:

(d) cooling a mixture comprising one or more of the double-stranded DNA fragments having linkers attached thereto as in step (c), which mixture optionally contains other double-stranded DNA fragments which have compatible termini for ligation and which code for repeating amino acid sequences to a temperature sufficiently low to allow ligation of said double-stranded DNA sequences into longer double-stranded DNA fragments; and (e) treating said cooled mixture of double-stranded DNA fragments with a ligase enzyme to covalently link said double-stranded DNA fragments to form linked double-stranded DNA fragments which code for contiguous repeats of one or more amino acid sequences.

Still another aspect of this invention relates to a method of forming a recombinant plasmid comprising a plasmid vector and one or more double-stranded DNA fragments as described above, said method comprising the steps of:

(a) cleaving a plasmid vector at a predetermined restriction site; and (b) enzymatically attaching one or more double-stranded DNA sequences at said site so as to maintain the genetic code reading frame of said DNA fragments relative to translation initiation DNA sequences in said plasmid vector and to maintain the repeating amino acid sequence through and between any joined DNA fragments, such that said sequences are under the control of a regulatable gene promoter sequence in said plasmid vector whereby said DNA sequence is expressible in said plasmid to form polypeptides composed of a known amino acid sequence when cloned into a microbial organism.

The invention also relates to recombinant plasmids and recombinant microorganisms formed by the process of this invention. The invention further relates to any of the polypeptide products of the recombinant processes of this invention.

DESCRIPTION OF THE PREFERRED EMBODIMENTS

One aspect of this invention relates to a process for forming double-stranded DNA fragments which code for a desired repeating amino acid sequence with linker DNA ends which may be inserted into a suitable plasmid vector. As part of the first step of the process at least two synthetic oligodeoxynucleotides which can function as coding or anticoding strands for a desired amino acid sequence are prepared. Oligodeoxynucleotides are polymeric DNA sequences which are linear chains of deoxynucleotides covalently linked through a phosphodiester bond between the C5' and C3' atoms of adjacent deoxyribose sugar moieties. The synthetic method for preparing such oligodeoxynucleotides sequences may vary widely. For example, they can each be chemically synthesized by any one of several available solution or solid phase techniques. See M.H. Caruthers et al., *Genetic Engineering, Volume* 4 (J. Setlow and A. Hollaender, eds.; Plenum Press, 1982) for a review of the preferred solid phase synthesis technology based on phosphoramidite chemistries as originally disclosed in S.L. Beaucage and M. Caruthers, *Tetrahedron Letters* 22, 1859–1862 (1981).

The nature of the synthetic oligodeoxynucleotides prepared for use in the practice of this invention is critical. The prepared oligodeoxynucleotides must consist of at least two oligodeoxynucleotides which are capable of base pairing and forming partially double-stranded DNA. Accordingly, at least one of the selected or prepared synthetic oligodeoxynucleotides must be a circularly permuted sequence of an oligodeoxynucleotide which is perfectly complementary to another of the selected and prepared oligodeoxynucleotides using the base pairing rules of guanine with cytosine and adenine with thymine well known in nucleic acid biochemistry and taking into account the antiparallel polarity of the two complementary synthetic oligodeoxynucleotide strands. Thus, for example, if one synthetic oligodeoxynucleotide is represented by the sequence:

5'-a-b-c-d-e.....f-g-h-3' where a, b, c, d, e, f, g and h each stand for one of the four purine or pyrimidine nucleotides, the other synthetic oligodeoxynucleotide might appear as 3'-d'-e'...f'-g'-h'-a'-b'-c'-5' with d and d', e and e' and the like, representing the appropriate paired bases. The choice of a circularly permuted sequence for at least one of the synthetic deoxynucleotides is restricted to those sequences which leave unequal numbers of paired bases and unpaired bases in either strand when the two synthetic oligodeoxynucleotides are annealed to one another in later steps of the method. It is further required that the number of unpaired bases following annealing not be zero. Thus, in the above-example, the number of bases represented by the sequence 5'-d e....f g h-3' is not equal to the number of bases represented by the sequence 5'-a b c-3'. The DNA sequences of the oligodeoxynucleotides are selected according to these rules in order to control the polar orientation of the unpaired bases following strand annealing (that is, the unpaired bases will either be on the 5' or 3' end of each synthetic deoxynucleotide following the annealing step in the current process) or to prevent hybridizations between at least two complementary oligodeoxynucleotide strands which might leave no unpaired bases and thereby prevent efficient oligomerization subsequent to or during the annealing step of the present invention.

The choice of nucleotide sequence in the synthetic oligodeoxynucleotides is governed by the order of amino acids in the basic repeating unit for which directly repeating oligomers are desired in product polypeptides. One or more of the synthetic oligodeoxynucleotides can then be selected to code for the desired basic repeating peptide unit or a circularly permuted version of this coding sequence. Coding sequences are chosen on the basis of the genetic code and preferred codon usage in the host microorganism in which the synthetic gene described in this invention is to be expressed. More than one coding sequence may be chosen in situations where codon preference is unknown or ambiguous for optimum codon usage in the chosen host microorganism. The length of the selected or prepared oligodeoxynucleotides may vary widely. The minimum length of the oligodeoxynucleotide for use in the process of this invention is a number of covalently joined nucleotides which is equal to three times the number of amino acids in the basic repeating peptide unit. The maximum length is not critical and the employment of synthetic deoxynucleotides with integral multiples of this number of bases is also acceptable and is preferred if the number of amino acids in the basic repeating peptide unit is less than about 4.

The synthetic oligodeoxynucleotides will generally terminate in a 5' hydroxyl chemical grouo and will require phosphorylation of the 5' chain end if this moiety does not already bear a phosphate chemical group. Phosphorylation of a 5' hydroxyl chain end can be conveniently done with any enzyme capable of transferring a phosphate chemical group preferably from adenosine triphosphate (ATP) to the 5' hydroxyl site. The preferred enzyme is T4 polynucleotide kinase (E.C. 2.7.1.78) but it is recognized that other phosphorylation enzymes such as phosphatases under the appropriate substrate conditions are also acceptable for the phosphorylation reaction.

As part of the initial step of this process, the phosphorylated oligodeoxynucleotides are annealed to form complementary oligomeric forms. These complementary synthetic oligodeoxynucleotides may be annealed by heating a mixture of two or more oligodeoxynucleotides, at least two of which are complementary, in an appropriate buffered salt solution. The final temperature to which the mixture is heated may vary widely, but is preferably above the temperature at which the synthetic oligodeoxynucleotides can stably form hydrogen bonds and base pair and below 100° C. The heated mixture of synthetic oligodeoxynucleotides is slowly cooled to a temperature allowing stable base pairs to form between complementary strands. For example, using the nomenclature introduced above, two of the possible resultant DNA hybrid duplex sequences can be represented as

$$5'\text{-}a\text{—}b\text{—}c\text{—}d\text{—}e \ldots f\text{—}g\text{—}h\text{-}3' \qquad (1)$$
$$3'\text{-}d' \ e' \ldots f' \ g' \ h'a'b'c'\text{-}5' \ \text{or}$$

$$5'\text{-}a\text{—}b\text{—}c\text{—}d\text{—}e \ldots f\text{—}g\text{—}h\text{-}3' \qquad (2)$$
$$3'\text{-}d'e' \ldots f'g'h'a' \ b' \ c'\text{-}5'$$

Other structures may be possible if there is internal sequence degeneracy in the synthetic oligodeoxynucleotides; these structures will possibly have no or at worst a few base pair mismatches. The number of structures formed will be a consequence of the smallest unique sequence contained within the oligodeoxynucleotides and the number of synthetic oligodeoxynucleotides in the reaction mixture. For example, if the sequence 5'-a-b-c-d-e...f-g-h-3' has no internal degeneracy and only two synthetic oligodeoxynucleotides are used, the two base pairing structures shown above will be the only product molecules of thermal annealing between the two synthetic oligodeoxynucleotides.

The preferred final temperature is chosen so as to allow only hybrid structures with a defined single stranded polarity (that is, only 5 or 3' base overhangs) to be formed, but other temperatures below this value can be used as long as the cooling step is sufficiently slow so as to allow complete formation of only the most stable base paired hybrid structures. Oligomeric forms of the overlapping synthetic DNA strands with individual synthetic oligodeoxynucleotides base paired in staggered fashion to two of the complementary and overlapping synthetic oligodeoxynucleotides will subsequently be formed by this method when the sample temperature is lowered further. Lowering of the sample temperature at this stage of the procedure will allow the staggered ends of the overlapping base paired synthetic oligodeoxynucleotides to further anneal and stably form base pairs with other combinations of overlapping base paired synthetic oligodeoxynucleotides. The length of hybrid duplex DNA segments resulting from annealing may vary widely. In the preferred embodiments of the invention the length of such fragments is generally substantial since the two synthetic oligodeoxynucleotides are selected such that they cannot hybridize in perfect register and thus they do not prematurely terminate duplex chain elongation before substantial lengths have been obtained. The oligomeric DNA strands produced during the annealing step will code for contiguous repeats of the basic repeating peptide unit chosen with the ends of the oligomeric DNA strands coding for some portion of the basic repeating peptide unit. By judicious choice of the annealing temperature and base sequence in the synthetic oligodeoxynucleotides, the oligomeric DNA strands will both have a 5' or both have a 3' overhanging end with the two ends being self-complementary. For example, using the nomenclature introduced above, an oligomeric duplex DNA produced by the annealing step of this process might appear as The number of annealed complementary synthetic oligodeoxynucleotides will vary between each set of stably base paired oligodeoxynucleotides and will form a distribution of sizes ranging from one to many repeating base paired and overlapping synthetic oligodeoxynucleotides per annealed set.

The above process has been described in terms of using two or more complementary oligodeoxynucleotides. Certain embodiments of the method of this invention may require more than two oligodeoxynucleotides to be annealed in preparation of oligomeric DNA fragments. Practice of such an embodiment may be preferred when optimal codon usage for a given host all for peptide or protein expression is unknown or ambiguous or when stringent translational control related to the amounts of transfer RNA (tRNA) molecules in a bacterial cell limits the rate or extent of protein synthesis. Combinations of more than one pair of complementary oligodeoxynucleotides can be annealed into oligomeric DNA fragments with complete base pairing according to the adenine-thymine and guanine-cytosine base pairing requirement if the unpaired bases between any given pair of annealed complementary oligodeoxynucleotides are equivalent in sequence and polarity to the unpaired bases in any or all other pairs of complementary synthetic oligodeoxynucleotides in the reaction mixture. For example, using the nomenclature introduced earlier, an example of two pairs of synthetic oligodeoxynucleotides which could be oligomerized as described above in which the unpaired bases a b c and a' b' c' are equivalent in sequence and polarity are:

It is also possible to use an odd number of synthetic oligodeoxynucleotides equal to or greater than three within the context of the present invention if all except one such synthetic oligodeoxynucleotide have a complementary oligodeoxynucleotide present as a circularly permuted sequence, and the remaining unpaired synthetic deoxynucleotide has a nucleotide sequence that varies at most at only a few positions from some other synthetic oligodeoxynucleotide in the reaction mixture. The base pair mismatches in this embodiment of the invention must still allow stable formation of duplex molecules through hydrogen bond formation upon annealing at an appropriate temperature. That is, the base pair mismatches in the resulting duplex molecules must be so few in number as to not destabilize duplex formation at the chosen annealing temperature.

In the second step of this embodiment of the invention, the oligomerized DNA strands are treated with a ligase enzyme to covalently link the base paired synthetic oligodeoxynucleotides which are oriented parallel with respect to their 5' to 3' polarity. The ligase enzyme used can be any of several enzymes capable of forming phosphodiester bonds between two DNA strands respectively terminating in 3' hydroxyl and 5' phosphate chemical groups. The preferred enzymes include T4 DNA ligase (E.C. 6.5.1.1) and *E. coli* DNA ligase (AND+, E.C. 6.5.1.2). These enzymes would be employed with appropriate cofactors and substrate or substrates in concentrations appropriate for good enzymatic activity using procedures known in the art. The cofactors for any ligating enzyme and most particularly for T4 DNA ligase can include the enzyme T4 RNA ligase (E.C. 6.5.1.3) which is known to stimulate formation of linear ligated DNA products in the presence of T4 DNA ligase (cf A Sugino et al., *Journal of Biological Chemistry* 252. 3987-3994 (1977)), or can include any of several nonspecific polymers such as polyethylene glycol, spermidine, Ficoll, or bovine serum albumin (cf. B.H. Pheiffer and S.B. Zimmerman, *Nucleic Acids Research* 11, 7853-7871 (1983)).

The double-stranded DNA molecules generated following enzymatic treatment with a DNA ligase enzyme may have one or more nicks or gaps in either or both of the DNA strands. These nicks or gaps can arise by several mechanisms such as incomplete deprotection of 5' or 3' chain ends of the synthetic oligodeoxynucleotides during chemical synthesis of said oligodeoxynucleotides, improper base pairing during the annealing step of the claimed process, contamination of the synthetic oligodeoxynucleotides with chains one or several bases shorter due to premature chain termination or elongation failure during chemical synthesis and subsequent inadequate purification of the desired synthetic oligodeoxynucleotide, incomplete chain ligation, incomplete addition of phosphate chemical groups to 5' hydroxyl chain ends, or nonspecific degradation of the synthetic oligodeoxynucleotides by a contaminating nuclease prior to or subsequent to the ligation step of the claimed process. Many if not all of these problems can be substantially reduced or eliminated by treatment of the ligated double-stranded synthetic DNA fragments with a DNA polymerase. The DNA polymerase will extend extant DNA chains in a 5' to 3' direction by the process of nick translation (cf. R.G. Kelly et al., *Journal of Biological Chemistry* 245, 39–45 (1970). The various DNA polymerases or fragments thereof known in the art are useful for this step in the claimed process with the preferred enzymes being *Escherichia coli* DNA polymerase I (E.C. 2.7.7.7) or any proteolytic fragment of *E. coli* DNA polymerase I which retains the polymerase activity of the holoenzyme.

Following treatment with a DNA polymerase, the synthetic double-stranded DNA fragments prepared in certain embodiments of the invention are fractionated to isolate only those fragments of greater than some minimum size for use in subsequent process steps. This purification procedure may also be necessary for any natural genes, gene fragments or DNA copies of messenger RNAs for specific genes or gene fragments which are of utility in certain embodiments of the process of this invention as described below. The method of purification can be chosen from a variety of biochemical techniques including size exclusion chromatography, ion exchange chromatography and affinity chromatography. The current preferred method is size exclusion chromatography over a suitable separation matrix; many such matrices are commercially available.

Any natural or synthetic double-stranded DNA fragment selected or prepared for the process of this invention is generally of a length which is sufficient to code for a polypeptide which has desirable polymeric properties. The selection of a particular polymeric property such as strength, elasticity, thermoplasticity, binding or coordination to other molecules, and the like, will determine more or less the proper relationship between length of polypeptide product and optimized structure-function activity of the polypeptide. However a general attribute of polymers is that increasing chain length usually enhances the physical property being optimized in the polymer to some degree. It is therefore generally desirable to maximize the size of double-stranded DNA fragment or fragments to be used in this invention within the exigencies of the molecular cloning aspects of this invention. Cloning of DNA fragments above some minimum size is also convenient for proposes of subsequently identifying bacterial hosts containing olasmid vectors which in turn contain the DNA fragments and for optimizing the ligation reaction of the natural or synthetic DNA fragment or fragments into the olasmid vector as described below. In the preferred embodiments of this invention, the length of the fragments is at least about 75 base pairs, in the particularly preferred embodiments of the invention the fragments are at least about 100 base pairs in length.

In the third step of the primary process of this invention, the ends of double-stranded synthetic or naturally occurring DNA fragments are modified prior to cloning. The ends of said DNA fragments are modified by attachment of a DNA linker with or without prior enzymatic treatment of the said DNA fragment to render the ends of said DNA fragment blunt-ended or flush. The ends of the synthesized double-stranded DNA fragments are made flush enzymatically using conventional techniques such as those described in T. Maniatis et al., *Molecular Cloning* (Cold Spring Harbor), pp. 113–114, and other like references. DNA linkers as defined for purposes of describing this invention are double-stranded oligodeoxynucleotides which contain at least one restriction enzyme recognition sequence or contain an end sequence for which any unpaired bases are equivalent to those found at an end of duplex DNA following the action of a specific restriction enzyme. The term adapters within the descriptive text of this specification is equivalent to the term DNA linkers. The attachment of DNA linkers to the double-stranded DNA fragments is carried out enzymatically with a suitable ligase enzyme, preferably AND-dependent *E. coli* DNA ligase or T4 DNA ligase. The resulting double-stranded DNA fragments with linkers attached may subsequently require exhaustive digestion with a restriction enzyme which has a recognition sequence within oligomeric forms of the linker DNA so as to limit the number of linker DNA molecules attached to any one end of a double-stranded DNA fragment to one linker molecule per end. The type of linkers selected for use with any particular double-stranded DNA fragment and/or olasmid vector as described below is critical to the process of this invention. The selected linkers must contain at their ends or internally at least one restriction enzyme recognition site which is not present within the repeating oligodeoxynucleotide sequence and which is preferably present only once within the olasmid vector into which the DNA fragment will be inserted. For example, if the repeating oligodeoxynucleotide sequences used to prepare a synthetic DNA fragment of the type described in this invention are (6)

which code for repeats of the amino acid sequence Glycine-Valine-Glycine-Valine-Proline (Gly-Val-Gly-Val-Pro in three letter amino acid code) when this double-stranded deoxynucleotide is oligomerized with itself, then the linker DNA molecule:

(7)

can be attached to oligomeric forms of the above pentadecanucleotide and subsequently cleaved with the restriction enzyme ApaI (recognition sequence GGG CCC) which will cut within the linker DNA molecules but not within the oligomeric forms of the pentadecanucleotide. These DNA fragments can then be inserted into a suitable olasmid vector with a unique ApaI restriction enzyme recognition site.

DNA linkers used in the practice of the process of this invention must have additional unique properties. For example, the nucleotide sequence contained within any DNA linker must allow for placement of the attached DNA fragment or fragments in the proper reading frame (as defined by the genetic code) relative to any controlling genetic element such as a translation initiation DNA sequence found in the plasmid vector into which the DNA fragment or fragments will be inserted. It is also preferable that the repeating amino acid sequence coding for any DNA fragment attached to a DNA linker be continuous into and within the amino acid sequence coded for by the DNA linker. For example, if the DNA fragment to which DNA linkers are to be attached is oligomeric forms of the sequence $$\begin{array}{l}\text{5'-GTT GGT GTT CCG GGT-3'}\\ \text{3'-CCA CAA CCA CAA GGC-5'}\end{array} \quad (8)$$

which in oligomeric form codes for repeats of the amino acid sequence Val-Gly-Val-Pro-Gly, then an adequate DNA linker within the context of this invention would be $$\begin{array}{l}\text{5'-GTT GGG GTG CCG GGT-3'}\\ \text{3'-CCA CAA CCC CAC GGC-5'}\end{array} \quad (9)$$

In this representative example, the linker DNA contains within it a unique recognition sequence for the restriction enzyme BanI (GGTGCC) which is not found within the DNA fragment described above and is preferably also not found in the plasmid vector into which this DNA fragment is to be inserted. This linker DNA further retains the ability to insure the reading frame of the DNA fragment will be maintained so as to code for repeats of the amino acid sequence val-Gly-Val-Pro-Gly and further continues the reading frame of the coding sequence into and through the linker DNA. That is, the linker DNA also codes for the amino acid sequence Val-Gly-Val-Pro-Gly.

It is additionally preferred that the single-stranded ends of duplex linker DNAs have self-complementary but not have equivalent sequences (that is, the end sequences do not have a two-fold rotational axis of symmetry) in order to ensure that they will only attach to the oligomerized DNA segments in the proper orientation for maintaining the genetic coding capacity for the desired repeating amino acid sequence for example, if the desired repeating amino acid sequence is coded for by the oligomerized nucleotide sequence shown as (3) above and the chosen DNA linker is $$\begin{array}{l}\text{5'-a—b—c—j—k—l—m—n } \ldots \text{ o—p—q-3'}\\ \text{3'-j'k'l'm'n' } \ldots \text{ o'p'q'a'b'c'-5'}\end{array} \quad (10)$$

then it is required that 5'-a-b-c not be equivalent to 5'-c'-b'-a'. This avoids DNA linker sequences which might attach with the wrong polarity to the oligomerized DNA and code for an undesirable amino acid sequence from an open reading frame on the anticoding strand. An example of such an anticoding strand is the sequence 5'-c'-b'-a'-q'-p'-o'...n'-m'-l'-k'-j'-3' shown in (10).

Two DNA fragments coding for different amino acid sequences may be joined to the same linker DNA in some aspects of this invention. In this instance, linker DNA is constrained to maintain the amino acid sequence of at least one of the sequences encoded by one of the two joined DNA fragments such that the fragment-linker-fragment DNA which either encodes a polypeptide chain with the repeating amino acid sequence encoded by each fragment covalently joined to a contiguous repeating amino acid sequence encoded by the other fragment or encodes a polypeptide chain that covalently joins and overlaps the two sequences at an amino acid residue or residues present in both repeating amino acid sequences. An example of DNA fragments within the scope of this invention which are joined by a linker DNA that provides overlap of the repeating amino acid sequences encoded respectively by each DNA fragment would be the DNA fragments formed as oligomers of the double-stranded deoxynucleotides $$\begin{array}{l}\text{5'-CCG CCG GGT CCG CCG GGT-3'}\\ \text{3'-CCA GGC GGC CCA GGC GGC-5'}\\ \phantom{\text{3'-}}\text{Pro Pro Gly Pro Pro Gly}\end{array} \quad (11)$$

and $$\begin{array}{l}\text{5'-GTT GGT GTT CCG GGT-3'}\\ \text{3'-CCA CAA CCA CAA GGC-5'}\\ \phantom{\text{3'-}}\text{Val Gly Val Pro Gly}\end{array} \quad (12)$$

which in turn can be joined by the DNA linker $$\begin{array}{l}\text{5'-GTT GGG GTG CCG GGT-3'}\\ \text{3'CCA CAA CCC CAC GGC-5'}\\ \phantom{\text{3'}}\text{Val Gly Val Pro Gly}\end{array} \quad (13)$$

In this representative example, the linker DNA contains a recognition sequence (GGTGCC) for the restriction enzyme Ban I which is not present in either oligomeric form of the double-stranded deoxynucleotides. The joined DNA fragments will code for a polypeptide which in part can be represented as the amino acid sequences (Pro-Pro-Gly)n-(Val-Gly-Val-Pro-Gly)m or (Val-Gly-Val-Pro-Gly)m-(Pro-Pro-Gly)n where the two repeating amino acid sequences overlap at a common Proline-Glycine dipeptide and the recognition sequence for Ban I has been introduced between the two original DNA fragments.

Several classes of linker DNA are preferred for use in the process of this invention. The DNA fragments to which DNA linkers are to be attached will have either blunt-ended or cohesive termini with the preferred class of DNA fragment ends being cohesive termini. Linker DNA for blunt-ended DNA fragments will preferably have at least one blunt end and will lead to DNA fragments with identical termini once the linker DNA is attached to the DNA fragments and subsequently cleaved by the appropriate restriction enzyme recognizing some unique site within the linker DNA. It is particularly preferred in this instance to use linker DNA with at least two non-overlapping restriction enzyme recognition sites that result in cohesive termini when any of the appropriate restriction enzymes cleave the linker DNA and for which the cohesive termini produced by any two appropriate restriction enzymes following cleavage are complementary for base pairing and non-equivalent. It is also particularly preferred to use linker DNA in the process of this invention which contains restriction enzyme recognition sites that are non-palindromic and are recognizable and cleavable by restriction enzymes with non-palindromic or multiple recognition sites. Illustrative examples of such enzymes are AccI, AflIII, AhaII, AvaI, BanI, BanII, BglI, HaeII, HgiAI, HincII, NspBII, XhoII, BbvI, BsmI, FokI, GsuI, HgaI, HphI, MboII, MnlI, SfaNI, SfiI, and TthIIII. The non-equivalence of the DNA fragment termini following attachment and cleavage of such DNA linkers provides that two or more of such DNA fragments or other DNA fragments with cohesive termini compatible for base pairing to one or both termini of such DNA fragments can only be attached unidirectionally to one another. The non-equivalence of the cohesive termini on such DNA fragments also insures that the repeating amino acid sequences encoded by covalently joined aggregates of two or more DNA fragments will be of the type and variety desired. That is, each of the DNA fragments and linker DNAs in such joined aggregates will be certain to express a polypeptide with the desired contiguous repeating amino acid sequence or sequences from the appropriate DNA coding strand and no DNA fragment or linker DNAs will be joined in the larger aggregate with the wrong polarity. Linker DNAs containing a number of restriction enzyme recognition sites can be used. Where a DNA linker contains at least one non-overlapping restriction enzyme recognition site, it is particularly preferred to use linker DNAs with two or less such recognition sites to minimize the size of the linker DNAs which are to be made synthetically, although some embodiments of the current invention may use linker DNA with more than two such recognition sites. DNA Linkers with at least two restriction enzyme recognition sites are cleaved sequentially with the appropriate restriction enzymes following attachment to DNA fragments to yield DNA fragments with non-equivalent cohesive termini.

Another class of embodiments which fall within the scope of the present invention are those where DNA linkers are attached to a plasmid expression vector to provide new insertion sites for double-stranded DNA fragments prepared and/or selected by the methods of the present invention. Such linkers can be attached to linearized olasmid DNA by techniques familiar to those practicing the art of molecular cloning and used as linkage sites for natural or synthetic DNA fragments bearing complementary DNA linker sequences.

It is also possible to combine the ligation reactions for any synthetic oligodeoxynucleotides being oligomerized and for linker DNAs being attached to oligomerized synthetic oligodeoxynucleotides in a single step within certain embodiments of the present invention. This approach offers several advantages including control of the size distribution of the synthetic genes by modulating the ratio of duplex oligodeoxynucleotides to linker DNAs. Another advantage is that any DNA chain which becomes circular during the oligodeoxynucleotide ligation step can subsequently be linearized to provide clonable DNA fragments as long as at least one linker DNA has been incorporated into this DNA fragment during enzymatic ligation.

In the ligation of DNA linkers to double-stranded DNA sequences, multimeric linker species are often formed. As used herein, multimeric species are those in which more than one linker is attached to the end of an oligomeric DNA sequences. In this event, the double-stranded DNA sequences are preferably subjected to exhaustive digestion with an appropriate restriction enzyme which has a recognition sequence within oligomeric forms of linker DNA so as to limit the number of linker DNA molecules attached to any one end of a double-stranded DNA fragment to one linker per end.

At this juncture the double-stranded DNA sequences with linkers attached to the ends can be cloned directly into a suitable restriction enzyme recognition site or pair of sites in a suitable replicable cloning vehicle and preferably in a olasmid vector. However, as noted above, there is a direct relationship between the length of the various double-stranded DNA fragments and the molecular weight of the polypeptide expressed from such fragments and there is also a direct relationship between the molecular weight of the polypeptide expressed from such fragments and the degree of quality of the desirable physical properties of the polypeptide product. Therefore, in the preferred embodiments of the invention it is often desirable to further increase the length of the DNA fragments prior to insertion into a plasmid vector. This increase in length can be conveniently obtained by mixing and cooling the DNA fragments with attached DNA linkers to a temperature sufficiently low to allow ligation of the DNA fragments through their linker ends into longer double-stranded DNA sequences which code for higher molecular polypeptides and then treating this mixture with a suitable ligase enzyme. The desirable temperature may vary widely, and in the preferred embodiments is above the freezing point of the mixture but sufficiently low to allow for maximum alignment of the linker ends of the double-stranded DNA fragments. In this preferred embodiment, the cooling step is also sufficiently slow so as to allow for the complete formation of the most stable aligned structures. After cooling, the mixture can be treated with a suitable ligase enzyme at this lower temperature, and optionally with a DNA polymerase to covalently link the aligned double-stranded DNA fragments into the desired longer sequences.

Two or more of the fragments may be joined together into larger DNA fragments which each have at least about 75 base pairs using conventional ligation procedures, as for example those described in T. Maniatis et al., *Molecular Cloning* (Cold Spring Harbor, 1982), pp. 243-246, incorporated herein by reference. The preferred ligase enzyme for this step of the invention is T4 DNA ligase. These larger, joined DNA fragments contain one or more repeating oligodeoxynucleotide sequences which can code for either the same or distinct repeating amino acid sequences, and they are joined so as to continuously maintain the genetic code reading frame for at least one of the repeating amino acid sequences through and between DNA fragments. The symmetry and placement of the joined DNA fragments in the larger DNA fragment may vary, leading to polypeptides encoded by such larger DNA fragments which are either random or alternating block peptide copolymers. The larger DNA fragment will preferably have cohesive termini and most preferably cohesive termini which are non-equivalent. Examples of preferred cohesive termini found on each end of any of the aforesaid larger DNA fragments with complementary and equivalent sequences are:

```
5'     C ... —GGG  CC-3'           (14)
3'-CCGGG ... —C        -5'

5'-AATTC ...G      -3'              (15)
3'-      G... CTTAA -5'
``` which can base pair with DNA termini left following cleavage with the restriction enzymes Apa I or Eco RI, respectively. Examples of preferred cohesive termini which are non-equivalent and non-palindromic include the following sequences which result from cleavage of linker DNA with restriction enzymes which have multiple recognition sequences:

-continued (17) 5'-    C ... GTGCC-3'   Bsp 1286
    3'-ACGGG ... C     -5'

As an alternative source of double-stranded DNA fragments for use in preparing larger DNA fragments, natural genes or gene fragments or complementary DNA copies of all or a portion of a natural gene in the form of double-stranded DNA fragments can be isolated by techniques well known in the art of molecular cloning. These DNA fragments are restricted to those which mostly or wholly code for repeating amino acid sequences with the possible exception of their end nucleotides on each DNA strand when the triplet grouping of nucleotide sequences required by the genetic code is taken into account. Illustrative of natural genes or gene fragments which are useful in the practice of this invention are those which code for part or all of any form or isolate of the proteins collagen, elastin, keratin, troponin C, any other intermediate filament protein (cf. E. Lazarides, *Nature* 283, 249–256 (1980)) or silk fibroin and which includes most or all of an amino acid sequence which exhibits some degree of repetitiveness within the protein sequence. The degree of repetitiveness can be judged by DNA or protein sequence homology using various theoretical techniques in peptide biology. See, for example, S.B. Needleman and C.D. Wunsch, *Journal of Molecular Biology* 48, 443–53 (1970), A.D. McLachlan, *Journal of Molecular Biology* 61, 409–424 (1971), and D. Eisenberq et al., *Proc. Natl. Acad. Sci. (U.S.A.)* 81, 140–144 (1984). Exemplary of useful complementary DNA copies in this invention are those resulting from reverse transcription and DNA strand copying from messenger RNA by an appropriate reverse transcription process and DNA strand copying process wherein the messenger RNA is transcribed from genes coding for proteins such as collagen, elastin, keratin, troponin C, any other intermediate filament, or silk fibroin. These illustrative lists are not meant to be inclusive of all proteins from which part or all of an appropriate double-stranded DNA fragment can be prepared in any of the processes of this invention. These natural DNA fragments will preferably be prepared for isolation using a restriction enzyme which leaves cohesive termini on the natural DNA fragments compatible with the cohesive termini on DNA fragments of synthetic origin. Alternatively, the ends of any natural DNA fragments preferably may be adapted or modified with an appropriate DNA linker or linkers which subsequent to attachment to the natural DNA fragments can either be uniquely cleaved with one or more restriction enzymes to reveal or intrinsically has one or more cohesive termini compatible with the cohesive termini of one or more synthetic DNA fragments.

The repeating amino acid sequences for which the shorter DNA fragments and larger DNA fragments code in the primary process of this invention may vary widely, depending on the shorter DNA fragments selected for joining. Some of the preferred amino acid sequences encoded by the shorter DNA fragments include, in three letter amino acid code, poly(Gly), poly(Ala), poly(Gly-Ala), poly(Ala-Lys), poly(Gly-Ala-Gly-Ala-Gly-Ser), poly(Gly-Ala-Pro), poly(Gly-Pro-Ala), poly(Gly-Pro-Pro), poly(Gly-Val-Gly-Val-Pro), poly(Gly-Lys-Leu-Glu-Ala-Leu-Glu), poly(Ala-Lys-Pro-Thr-Tyr-Lys), poly(Ala-Lys-Pro- Ser-Tyr-Pro-Pro-Thr-Tyr-Lys) and the like wherein each amino acid residue has the L-amino acid conformation. Hydroxylated forms of any of these sequences are also preferable within certain embodiments of this invention. Some embodiments of this invention preferably select shorter DNA fragments which in part code for proline-containing or proline-rich amino acid sequence in which the DNA fragment-linker junction in oligomerized and larger DNA fragments occurs at or adjacent to a codon for the amino acid proline.

The DNA fragments or larger DNA fragments which code for the desired repeating amino acid sequence or joined repeating amino acid sequences can be inserted into a suitable olasmid vector using conventional techniques. Such techniques are well known in the art, and will not be described herein in detail. The larger DNA fragment will preferably be inserted at a unique site or pair of sites in the olasmid vector that allows perfect base pairing with cohesive termini on the larger DNA fragment. Such insertion may or may not yield a restriction enzyme recognition sequence at any of the junctions between the plasmid vector and the inserted DNA fragment. In the preferred embodiments of this invention such a restriction enzyme recognition sequence is constituted or reconstituted so that the inserted DNA fragment may be removed at a later time if desired in other applications of this invention. The site of DNA fragment insertion is preferably at a position 3' to a strong promoter/operator sequence in the plasmid vector which will regulate the production of sufficient amounts of polypeptide from the inserted DNA fragment which must be inserted in the correct reading frame and in the proper orientation. Illustrative of suitable plasmid vectors are pASl (described in U.S. Pat. No. 4,578,355), pKC30 (described in R. N. Rao, *Gene* 31, 247–250 (1984)) and oKN403 (described in U.S. Pat. No. 4,495,287). Preferred olasmid vectors include oJL6 (described in J.A. Lautenberger et al., *Gene* 23, 75–84 (1983), oAV1 whose construction is described below, ptac12H (described in E. Amann et al., *Gene* 25, 167–178 (1983)) and pKK233-2 (described in E. Amann and J. Brosius, *Gene, in press)*.

The plasmid vector plus the inserted DNA fragments or larger DNA fragment or fragments can be transformed using conventional techniques known in the art of molecular cloning using an acceptable bacterial host or other suitable microorganism in which the fragments are able to be expressed using established techniques, as for example those techniques described in U.S. Pat. No. 4,237,224; T. Maniatis et al., *Molecular Cloning: A Laboratory Manual* (Cold Spring Harbor, 1983), pp. 249–255; and D. Hanahan, *Journal of Molecular Biology* 166, 557–580 (1983) and incorporated herein by reference. Useful bacterial species may vary widely and may be strains of such well known species as *Escherichia coli, Bacillus subtilis* and the like. Preferred bacteria are strains of *E. coli* which are recombinant-deficient in order to prevent recombination events that may be favored between various segments of the inserted DNA fragments which have a substantial degree of internal repetitiveness. Especially preferred strains of *E. coli* are genotype rec A$^-$, especially MH01 (genotype recA$^-$, Tet$^r$ derivative of strain N99) whose construction is described in the examples below, MH03 (recA$^-$, Tetr derivative of strain N4830 made by P1 transduction from strain N6240 by techniques analogous to those used in the construction of MH01) DC1138 (pro$^-$, leu$^-$, λΔsrlR recA301::Tn 10, λdef cI$^+$), DC1139A (same as DC1138 except λdef ΔBam H1 ΔH1 cI857), JM109 and DHB9 (F' lacf'Z+Y+, recA, srl::Tn 10, phoR, ΔphoA, ΔmalF, {ara leu, Δlac, galE, galK; derived from MC1000).

After transformation, clonal isolates of transformed bacteria can be screened and selected using conventional techniques as for example screening by hybridization techniques using a radiolabelled synthetic oligodeoxynucleotide probe. The screened bacterial colonies can be selected and isolated once it is determined that they contain useful plasma d vectors, and can be assayed for expressing the inserted DNA as a polypeptide with the desired repeating amino acid sequence. If the cloned bacteria are capable of polypeptide expression from the DNA fragments utilized in the process of this invention, additional bacteria can be grown under fermentation conditions and these bacteria can be induced to express the desired polypeptide under conditions which are appropriate for the particular plasmid vector-bacterial host gene expression system being utilized. The desired polypeptide can then be isolated from the bacterial growth medium or from the bacteria using appropriate procedures. Illustrative of useful bacterial growth and bacterial product harvest procedures are those described in greater detail in European patent application 0131843 which is incorporated herein by reference.

If the cloned bacteria do not produce the polypeptide having the desired length or the desired repeating amino acid sequence, larger DNA fragments coding for an appropriate length polypeptide or one of the appropriate sequence can be obtained by isolation of one or more of the DNA fragment inserts from bacteria harboring a plasmid vector containing such insert using one or a pair of restriction enzymes which only cleave the associated linker DNAs and by oligomerization of such insert DNAs. The techniques for oligomerization and transformation of the newly created larger DNA fragment are obvious extensions of techniques described above in detail. This procedure can be applied to the creation of hybrid DNA fragments containing more than one DNA fragment coding for distinct repeating amino acid sequences. The oligomerization and recloning of DNA fragments can be done several times and can be continued until gene constructs having the described characteristics are formed. For example, individual DNA fragments coding for repeating amino acid sequences (Gly-Pro-Pro) and (Gly-Val-Gly-Val-Pro) can be joined in various recloning procedures to obtain random or alternating block copolymers polypeptides composed of repeating units of these amino acid sequences of various lengths. The sequence (Gly-Pro-Pro)n is an analogue to the eucaryotic protein collagen and may therefore form triple helical macromolecular aggregates and exhibit physical properties of high tensile strength and low elasticity. The sequence (Gly-Val-Gly-Val-Pro)m is a consensus sequence extracted from the known amino acid sequence of the eucaryotic protein elastin and has among its various physical properties the quality of elasticity. A hybrid copolymer polypeptide of these two repeating amino acid sequences might therefore be expected to show degrees of tensile strength and/or elasticity depending upon the nature and size of the larger DNA fragment prepared by the process of this invention which encodes the relevant hybrid copolymer polypeptide.

The process of this invention has many uses. For example, the process can be used to make or create bacteria which produce many useful polypeptide products. Illustrative of such products are analogues to naturally occurring proteins such as collagen, elastin, keratin, protein or glycoprotein elements of thick, intermediate or thin filaments in higher organisms, silk fibroin, tropomyosin, troponin C, resilin, eucaryotic egg shell proteins, insect cuticle proteins or other eucaryotic architectural proteins.

The following examples are presented to more particularly illustrate the invention and are not to be construed as limitations thereon.

EXAMPLE 1

Preparation of a Synthetic Gene for a Collagen Analogue Without DNA linkers.

The following complementary and overlapping oligodeoxynucleotides were prepared using solid phase phosphoramidite chemistry as disclosed in Beaucage and Caruthers, op. cit., on an Applied Biosystems model 380 DNA synthesizer:

| | |
|---|---|
| 5'-CG GGT CCG CCG GGT CCG C-3' | A. |
| 3'-GGC CCA GGC GGC CCA GGC-5' | B. |

Each oligodeoxynucleotide was isolated from shorter chain-elongation failure products by electrophoresis on and elution from 20% polyacrylamide gels containing 8 M urea. The final product was greater than 95% pure as determined by densitometry of autoradiograms prepared from end-labeled oligodeoxynucleotide products separated by analytical gel electrophoresis. Phosphate was added to the 5' ends of oligodeoxynucleotides A and B in separate reactions that contained 8.6 nmol oligodeoxynucleotide and 20 units T4 polynucleotide kinase in 35–45 ul buffer (66 mM Tris-HCl, oH 7.6, 1 mM spermidine, 10 mM MgCl$_2$, 15 mM dithiothreitol, 200 ug/ml bovine serum albumin (BSA), and 1 mM [$\gamma$-$^{32}$P]ATP with a specific activity of 0.2 Ci/mmol). These reaction mixtures were incubated for 2 hr at 37° C., then they were combined and were incubated at 14° C. overnight. During this time, oligodeoxy nucleotides A and B were annealing, presumably to form 17 base pair heteroduplexes with one base pair overhanging 3' ends or 10 base pair heteroduplexes with 8 base pair overhanging 5' ends. T4 DNA ligase (40 units) was added and incubation was continued at 14° C. for three days to polymerize the annealed oligodeoxynucleotides into long repetitive heteroduplex DNA coding for multiple repeats of the tripeptide (Gly-Pro-Pro). These synthetic genes were dialyzed against TE buffer (10 mM Tris-HCl, pH 7.5, 1 mM EDTA) to remove unincorporated oligodeoxynucleotides and buffer components. The ends of the synthetic genes were then blunt-ended by using three units of the Klenow fragment of E. coli DNA polymerase I in a reaction (50 ul total volume) containing the following: 600 uM each of dCTP, dGTP, dATP and TTP; 50 mM Tris-HCl, oH 7.8; 9mM MgCl$_2$; 10 mM 2-mercaptoethanol; and 50 ug/ml BSA. This reaction mixture was incubated at 14° C. for 30 minutes, then Na3EDTA was added to 10 mM and 150 ul of TE buffer was also added. The synthetic genes were purified on a DE-52 column, then ethanol precipitated. These synthetic genes were combined with the excluded fraction of another batch of synthetic genes prepared in substantially like manner that had previously been passed over a Sepharose 6B (Pharmacia) column. The combined synthetic genes were size fractionated on a Sepharose 4B (Pharmacia) column. The size distribution of synthetic genes was determined by electrophoresis on a 5% polyacrylamide gel.

The relative molecular weight distribution of fractions enriched for highly polymerized synthetic genes was compared on denaturing (i.e., containing 8 M urea) and non-denaturing 5% polyacrylamide gels. These gels showed the molecular weight distribution of single-stranded synthetic genes was smaller than expected from the molecular weight distribution of heteroduplex synthetic genes, suggesting that nicks and/or gaps were present in the double-stranded heteroduplex DNA. The nicks and/or gaps in 1.2 ug of synthetic genes were nick-translated *in vitro* using one unit of *E. coli* DNA polymerase I in the presence of 167 uM of each of dCTP, dGTP, dATP and TTP (with other buffer components as described in the blunt-ending reaction above) at 10° C. for 20 minutes (15 ul total volume).

Synthetic genes (0.5 ug heteroduplex DNA) were ligated without further manipulation to ClaI-digested and blunt-ended pJL6 plasmid DNA (2.0 ug) using five units of T4 DNA ligase in the buffer described above for the kinasing and ligation reactions (10 ul total volume). The reaction mixture was incubated overnight at 14° C., diluted to 200 ul in TE buffer, and used directly to transform E. coli strain MH01.

EXAMPLE 2

Bacteriophage P1 Transduction of *E. coli* strain N99cI+ and Construction of strain MH01.

In order to insure that any highly repetitive synthetic gene would not be excised from an expression vector by host-mediated homologous recombination, a recA mutation was introduced into the *E. coli* strain N99cI+. The recA mutation used here originated from *E. coli* strain N6240(CR63 recA::Tn1+0) This mutation was transferred into strain N99cI+ using the generalized transducing phage P1 cml, clr100. This particular phage carries a gene for chloramphenicol resistance (cml) and makes clear plaques (clr) at high temperature (42° C.) but turbid plaques at low temperature (32° C.). A high titer stock of P1 cml, clr100 grown on N6240 was used to transduce the recA mutation into N99cI+ as disclosed in J. H. Miller, *Experiments in Molecular Genetics* (Cold Spring Harbor, 1972). Five ml of a fresh overnight culture of N99cI+ was resuspended in an equal volume of MC buffer (0.1 M MgSO4, 5 mM CaCl2). The cells were then aerated at 37° C. for 15 minutes. A 100 ul aliquot of the suspended cells was added to 100 ul of a $10^{-1}$ or $10^{-2}$ dilution of the P1 lysate. After incubation at 37° C. for 20 minutes, 200 ul 1 M sodium citrate was added to each tube. The contents were then plated on LB plates containing 12.5 µg/ml tetracycline using 3 ml R top agar and the plates were incubated overnight at 39° C. Each tetracycline-resistant colony was screened for chloramphenicol sensitivity at 30° C. in order to ensure that it was not a fortuitous P1 lysogen. The presence of the recA mutation was confirmed by testing for sensitivity to UV light. Each potential bacterial transductant was streaked across an LB plate and different sections of the streaks were exposed to UV light for 0, 10 or 20 seconds, respectively. The agar plate was subsequently incubated at 30° C. overnight. One strain which was unusually UV sensitive relative to its parent (as demonstrated by growth only in the 0 second exposure section of the streak) was saved and designated MH01.

EXAMPLE 3

Transformation of MH01 with the Identification of Plasmids Bearing a Synthetic Collagen Analogue Gene Without DNA Linkers.

Frozen competent cells were prepared and transformed according to the Hanahan procedure (disclosed in D. Hanahan, *Journal of Molecular Biology*, 166: 557–580 1983) except the FSB buffer contained 10 mM potassium acetate, pH 6.4, 100 mM KCl, 15 mM MnCl2, 10 mM CaCl2, and 3 mM hexamine cobalt chloride. About 125 ng of DNA was used for each transformation; cells were subsequently selected for resistance to ampicillin and tetracycline. Transformants were replica plated onto nitrocellulose filters and those containing plasmids carrying synthetic gene inserts were identified by colony hybridization using radiolabeled oligodeoxynucleotide A as a probe. Hybridization was done at 37° C. for 2 hr in a solution composed of 20% formamide, 5X SSC, 0.1% SDS, 1 mM Na2EDTA, 1X Denhardt's solution, and 250 ug/ml denatured, sheared salmon sperm DNA. Nitrocellulose filters were washed three times with 5X SSC, 0.1% SDS at 55° C. successively for 20, 10, and 1 minute and then rinsed once in 2X SSC for two minutes at room temperature. Insert-bearing plasmids were subsequently isolated from bacterial clones yielding positive hybridization signals. These plasmids were restricted with the enzymes HindIII and NdeI, and the restriction products were analyzed by agarose gel electrophoresis to determine the size of the insert.

EXAMPLE 4

DNA Sequencing of 5' and 3' Junctions for Synthetic Collagen Analogue Genes in pJL6 and Identification of pACl Direct sequencing of the 5' junctions of the synthetic gene insert in several supercoiled plasmid DNAs bearing a synthetic collagen analogue gene without DNA linkers was conducted as disclosed in R. J. Zagursky et al., *Gene Analytical Techniques* 2: 289–94 (1985). The 5' and 3' gene orientations as used here respectively refer to the proximal and distal junctions relative to the lambda PL promoter located in pJL6. The following oligodeoxynucleotide was prepared by solid phase automated synthesis for priming DNA sequencing reactions based on the Sanger dideoxynucleotide sequencing method as adapted by Zagursky et al.:

5'-CTTACATATGGTTCGTGCAA-3'    C.

Primed synthesis reactions using this oligodeoxynucleotide allow sequencing into any gene inserted at the ClaI site of pJL6 and in a direction reading toward the HindIII site of oJL6. On the basis of proper reading frame and correct coding information at both the 5' and 3' junctions, one of these plasmids was designated pACl and investigated further.

For determining the junction sequence at the 3' end of the synthetic collagen analogue gene in pACl, the chemical cleavage method (as disclosed in Maxam and Gilbert, 1980, *Methods Enzymol.*, 65:499–560) was used after restricting ACl with HindIII, radiolabeling the linearized plasmid with [$\gamma$-$^{32}$P]ATP using T4 polynucleotide kinase, digesting the labeled plasmid DNA with the enzyme Nde I, and purifying the synthetic gene fragment on a 5% polyacrylamide gel containing 8 M urea.

EXAMPLE 5

Northern Blot Analysis of pACl-Encoded Collagen Analogue Gene Messenger RNA

Total RNA was prepared from the following three strains: DC1139A (pro leu r⁻m⁻ ΔSrlR-recA301::Tn10 λdef ΔBamHI ΔHl cI857), DC1139A(oJL6), and DC1139A(oACl). Cultures were grown in 20 ml LB broth at 30° C. overnight to OD600 = 3. Then the cultures were solit and half was shifted to 41° C. for 1 h in order to activate the λPL promoter. Following the induction, the cultures were chilled to 0° C. The cells were centrifuged at 8000X g for 5 minutes at 0° C. The pellets were resuspended in 500 ul STE buffer (100 mM NaCl, 10 mM Tris-HCl, pH 7.0, 1 mM Na2EDTA) and transferred to a 1.5 ml Eppendorf centrifuge tube. A 500 ul sample of hot (65° C.) phenol equilibrated with distilled water was added, the tube was vortexed and then the tube was incubated at 65° C. for 10 minutes. After a 5 minute centrifugation in an Eppendorf microfuge, the aqueous phase was removed and 500 ul of hot phenol was added. Another 500 ul of STE buffer was added to the first phenol phase, both tubes were vortexed, and both tubes were incubated at 65° C. for 5 minutes. Following another 5 minute centrifugation, both aqueous phases were pooled. The phenol extraction was repeated three more times. A final extraction was made with phenol:chloroform (1:1) at room temperature. The samples were extracted with ether and the RNA was precipitated with ethanol. The RNA was redissolved in 300 ul RNA storage buffer (210 ul 100% ethanol, 90 ul RNA buffer consisting of 20 mM sodium phosphate, pH 6.5, 1 mM Na2EDTA, 99.5% ethanol). The quality of the RNA preparation was monitored by electrophoresing 2 ul of the samples on a 1.2% agarose gel in 10 mM sodium phosphate buffer, pH 7.0. The OD260 and OD280 of each sample was recorded.

About 20 ug of each RNA sample was prepared for gel electrophoresis as disclosed in T. Maniatis et al., *Molecular Cloning* (Cold Soring Harbor, 1982), pp. 202-203. The RNA samples were electrophoresed on a 1.0% agarose-formaldehyde gel at 30 V. overnight. The next morning, the gel was stained with acridine orange to visualize the RNA and processed for Northern hybridization analysis according to the procedure disclosed by Barinaga et al. in *Transfer of RNA to Solid Supports* (Schleicher and Schuell). The agarose-formaldehyde gel was blotted onto DBM paper overnight. Northern prehybridization solution was prepared as described by Barinaga et al. The DBM paper with transferred RNA was incubated in 17 ml prehybridization solution at 42° C. overnight. The probe for the Northern blot consisted of oligodeoxynucleotide B of Example 1 radiolabeled with T4 polynucleotide kinase in the presence of [γ-$^{32}$P]ATP. The hybridization solution consisted of 25% formamide, 5X SSPE, 0.05% SDS, 1 nM Na2EDTA, lX Denhardt's solution and 750 ug/ml salmon sperm DNA (see T. Maniatis et al., op. cit., for definition of lX SSPE). The probe and hybridization solution were mixed and incubated with the DBM paper containing transferred RNA at 37° C. overnight. The DBM paper was then washed successively in 1 1 4X SSPE, 0.1% SDS for 20 minutes at 55° C., 800 ml minutes at 55° C,,200 ml of 4X SSPE for 1 minute at 55° and 500 ml of 2X SSPE at room temperature for 2 minutes. The blot was subsequently dried and exposed to X-ray film overnight. The autoradiogram resulting from this exposure showed very strong probe hybridization to DC1139A(pACl) RNA for the culture induced at 41° C. Hybridization in all other strains and under other culture conditions including growth of DC1139A(pACl) at 30° C. was minimal. These data demonstrate unambiguously that strong induction of collagen analogue oligodeoxy-nucleotide B-specific messenger RNA synthesis from the λP$_L$ promoter occurred only at the high temperature and only in strain DC1139A(pACl) as expected.

EXAMPLE 6

In Vitro Coupled Transcription-Translation Assay for pACl

A commercially available coupled transcription-translation system (Amersham) was used to investigate the proteins encoded by plasmid pACl. The reaction mixtures contained 2 5 ug of plasmid DNA and were prepared according to the procedure supplied by the manufacturer. The parent plasmid pJL6 was studied in parallel reactions for comparison with pACl. Following the in vitro transcription-translation stimulated by these plasmid DNAs, a portion of one sample containing pACl DNA was treated with 5 ug collagenase in 60 mM CaCl$_2$ at 37° C. for 30 minutes.

Each reaction mixture was diluted with an equal volume of loading buffer (0.08 M Tris-HCl, pH 6.8, 0.1 M dithiothreitol, 2% SDS, 10% glycerol, 0.1 mg/ml bromophenol blue) and heated to 100° C. for 5 minutes. Half of each sample was then electrophoresed on a 12.5% SDS-polyacrylamide gel at 50 V. overnight. Molecular weight marker proteins run in a parallel lane were bovine serum albumin, ovalbumin, carbonic anhydrase and cytochrome C. The gel was then fixed and flourographed with En[3] Hance using the procedure disclosed in *A Guide to Autoradiography Enhancement* (New England Nuclear). After exposure of the gel to X-ray film overnight, two prominent bands could be visualized on the autoradiogram. The first band occurred in the lane containing pJL6 DNA as well as the lane containing oACl DNA. This probably represents the beta-lactamase enzyme which is coded for by both plasmids. The second band is unique to pACl DNA and is a protein of 22,000 daltons based on its electrophoretic mobility. This protein is the product of the synthetic collagen analogue gene in pACl. Supporting evidence for this conclusion is the fact that the band is no longer visible in the sample containing pACl DNA and treated with collagenase prior to electrophoresis.

EXAMPLE 7

Peptide Expression from the Synthetic Collagen Analogue Gene Without DNA Linkers Contained in Plasmid pACl The in vivo expression of a collagen analogue peptide encoded by the synthetic gene inserted in the plasmid pACl was demonstrated using a whole-cell labeling protocol. Overnight cultures were prepared of DC1139A(pJL6) and DC1139A(oACl) at 30° C. The next morning, one ml of overnight culture was inoculated into 20 ml LB broth (10 g tryotone, 5 g yeast extract and 5 g NaCl in one liter of water) containing 50 ug/ml of ampicillin. The cultures were grown to OD600=0.4 at 30° C. One ml samples were then taken and washed twice in M63 salt solution. The pellets were resuspended in 1 ml M63 medium plus 0.2% glucose, 1 ug/ml of vitamin Bl, and 100 ug/ml of all amino acids except proline. The cultures were preincubated at 41° C. for 20 minutes before 2 uCi of [$^{14}$C]proline were added to each culture tube and the incubations were continued for an additional 3 minutes. About 1 mg of unlabeled proline was then added to all cultures, incubation was continued for an additional 3 minutes and then the incubations were terminated by pelleting the cells from all cultures. The cell pellets were washed once in 1 ml M63 salts to remove any residual unincorporated [$^{14}$C]proline. The final cell pellets were resuspended in 50 ul SDS loading buffer (80 mM Tris-HCl, oH 6.8, 100 mM dithiothreitol, 2% SDS, 10% glycerol, 100 ug/ml of bromohenol blue) and were immediately heated in a boiling water bath for 5 minutes. Aliquots of 20 ul were then electrophoresed on a 12.5% SDS-polyacrylamide gel. The resulting gel was then treated with En$^3$Hance (New England Nuclear) and exposed to X-ray film overnight. The resulting autoradiogram showed a protein band in the lane containing pACl proteins which was absent in the lane with pJL6 proteins; this band represented a protein with an apparent molecular weight of 22,000 daltons based on electrophoretic mobility. This protein was therefore of the same size as the pACl-specific protein band identified in the coupled transcription-translation system of Example 6.

The effect of temperature during culture preincubation was also determined. The experimental protocol was the same as above except that the temperature of preincubation was studied at temperatures ranging between 30° and 47° C. The resulting autoradiogram demonstrated that the temperature of preincubation leading to maximal collagen analogue peptide expression lies between 41° and 44° C.

There appeared to be an inconsistency between measured molecular weight of the collagen analogue encoded by pACl (22,000 daltons) and the calculated molecular weight of 12,000 daltons derived from physical mapping and DNA sequencing data for pACl. An experiment was therefore undertaken to determine whether or not the collagen analogue was migrating anomalously on SDS-polyacrylamide gels. Three SDS-polyacrylamide gels with 10%, 12.5% or 15% polyacrylamide concentrations were prepared and replicate samples from thermally induced DC1139A(pACl) cultures labeled with [$^{14}$C]proline as well as radiolabeled marker proteins were electrophoresed on all three SDS-polyacrylamide gels. The results indicate that the synthetic collagen analogue peptide migrates abnormally slow relative to the marker proteins. Therefore, the true molecular weight of the collagen analogue peptide is less than 22,000 daltons.

It was also of interest to us to determine whether or not the collagen analogue peptide segregates into the soluble or insoluble protein fraction of the cell since many genetically engineered proteins form insoluble aggregates termed inclusion bodies. A gently lysis procedure was performed and the proteins present in a high salt pellet as well as in the associated supernatant were analyzed. Two 1 ml samples of DC1139A(pJL6) and DC1139A(pACl) were labeled with [$^{14}$C]proline as described above following induction at 41° C. for 1 h. One sample of each culture was processed as before and represented the unfractionated extract. The other portions were pelleted following the pulse-chase and were washed with 1 ml TES buffer (40 mM Tris-HCl), pH 8.0, 1 mM EDTA, 25% sucrose). The pellets were resuspended in 250 ul TES buffer and 1 mg of lysozyme was added. The samples were frozen in dry ice and thawed in a 37° C. water bath two times in order to facilitate lysis. Lysis buffer was subsequently added to the following concentrations: 0.5% Nonidet P40, 10 mM MgCl$_2$, 50 mM NaCl. The viscosity of the cell lysates was reduced by addition of *E. coli* DNase I enzyme to 20 ug/ml. The sample were then placed on ice for 30 minutes and were centrifuged in an Eppendorf microfuge for 10 minutes at 4° C. The resulting supernatants had trichloroacetic acid added to a final concentration of 10% and were placed on ice for 15 minutes. These acidified samples were centrifuged (again for 10 minutes at 4° C.) and the white pellets were washed two times with 100% ethanol before being resuspended in 50 ul SDS loading buffer and being heated in a boiling water bath for 5 minutes. The high salt pellets were washed once in TES buffer before being resuspended and heated in SDS loading buffer. Sufficient amounts of 1 M Tris-HCl, pH 8 0, were added to those samples with a yellow hue to return their color to blue prior to heating in the boiling water bath. The fractionated samples as well as the unfractionated control samples were electrophoresed on a 12.5% polyacrylamide gel, treated with En$^3$ Hance and exposed overnight to X-ray film. The autoradiogram of this gel revealed that the major band at an apparent molecular weight of 22,000 daltons specifically found in the lanes containing DC1139A9(pACl) proteins was primarily found in the supernatant fraction and was the main labeled band in this lane.

EXAMPLE 8

Preparation of the Expression Vector pAvl

Genes inserted in the expression vector oJL6 at the ClaI site, when expressed, produce proteins that are fusion peptides containing the first 13 amino acid residues of the λcII protein. A new expression vector was designed and constructed that removes the protein coding sequences related to the cII protein from oJL6 and also introduces a unique ApaI restriction endonuclease recognition site; this new expression vector was designated pAVl. The plasmid oAVl still makes use of the λPL promoter and a variant of the DNA sequences just upstream of the translational initiation codon for that portion, but the plasmid vector DNA between the NdeI and HindIII sites of pJL6 have been replaced with a chemically synthesized DNA sequence that allows the tripeptide Met-Gly-Pro to be made rather than the first 13 amino acids of the λcII protein. The new ApaI restriction endonuclease recognition site is located within this sequence such that the DNA encoding the amino acid residue Pro is cleaved. Any synthetic or natural gene or gene segment terminating in the unpaired base sequence...GGCC-3' can be cloned into the Apa I site of pAVl, and, upon expression of the gene, the aforementioned tripeptide will comprise the amino terminus of the peptide produced under the control of the PL promoter in pAVl.

The following oligodeoxynucleotides were synthesized as the first step in constructing pAVl using an Applied Biosystems model 380A automated DNA synthesizer:

5'-TAAGGAAATACTTACATATGGGGCCCTAAGCTTTAATGCGGTAGTT-3'    D.

5'-TAAAGCTTAGGGCCCCATATGTA-3'  E.

The oligodeoxynucleotide E is completely complementary to a portion of the oligodeoxynucleotide D and produces a DNA fragment having both 5' and 3' overhanging ends. When annealed, oligodeoxynucleotides D and E form a heteroduplex DNA within which are located restriction enzyme recognition sites for both NdeI and HindIII. The most direct method of constructing oAV1 from D and E is to digest the synthetic heteroduplex with NdeI and HindIII and then ligate the heteroduplex product into pJL6 from which the small DNA fragment produced by an NdeI-HindIII double digest has been excised. During the course of constructing pAV1, it was determined that NdeI restricted the synthetic heteroduplex formed by D and E poorly or not at all, necessitating the additional steps described herein. Oligodeoxynucleotides D and F were annealed (270 pmol of each) in 35 ul of 10 mM TE buffer (see Example 1) by allowing the solution to cool slowly from 75° C. to room temperature. A portion of this synthetic heteroduplex was radiolabeled by T4 polynucleotide kinase in the presence of [λ-$^{32}$P]ATP. After completing the radiolabeling, the synthetic heteroduplex was purified by chromatography on DE-5$_2$ cellulose (Whatman) and then precipitated in ethanol. The labeled synthetic heteroduplex was added to the unlabeled material as a tracer and the combined fractions were further purified on a NENSORB-20 column (DuPont) and then concentrated by evaporation. Another 270 pmol each of oligodeoxynucleotides D and E were added to the concentrated solution and the annealing reaction was repeated by allowing the solution to cool slowly from 98° C. to 4° C. Proper annealing was monitored by gel electrophoresis of an aliquot of the reaction mixture in 16% polyacrylamide.

The synthetic heteroduplex was restricted at 37° C. for 5 h with 75 units of HindIII restriction enzyme in 50 mM NaCl, 50 mM Tris-HCl, oH 8.0, 10 mM MgCl$_2$, and 100 ug/ml BSA. Then nine units of NdeI enzyme were added (after adjusting the buffer components to 200 mM NaCl, 60 mM Tris-HCl, pH 8.0, 17 mM MgCl$_2$, and 200 ug ml BSA) and incubation at 37° C. was continued overnight. The reaction mixture was stored at −20° C. and subsequently 7.5 units of HindIII enzyme and 3 units 5 of NdeI enzyme were added and the mixture was again incubated overnight but at room temperature. The reaction mixture was then extracted twice with phenol:chloroform (1:1), once with ether, and then was purified by chromatography through Sephadex G-25 (Pharmacia). The excluded fractions were pooled and the synthetic heteroduplex was again restricted with 15 units NdeI enzyme at room temperature for 24 h in 150 mM NaCl, 10 mM Tris-HCl, oH 7.8, 7 mM MgCl$_2$, 6 mM 2-mercaptoethanol, and 100 ug/ml BSA. The reaction mixture was extracted once with phenol:chloroform (1:1), and the synthetic heteroduplex was further purified by chromatography on Sephadex G-25 (Pharmacia). The excluded fractions were again pooled and then treated with 100 units of HindIII enzyme for 24 h at room temperature in 50 mM NaCl, 50 mM Tris-HCl, pH 8.0, 10 mM MgCl$_2$, and 100 ug/ml BSA. This incubation was followed by extraction of the reaction mixture with phenol:chloroform (1:1) and the synthetic heteroduplex was purified by chromatography through Sephadex G-25 (Pharmacia). The excluded fractions were pooled, and a portion of the pooled fractions was analyzed on either denaturing and non-denaturing 16% polyacrylamide gels either in the presence or absence of 8 M urea, respectively.

An alicuot of the cooled material representing approximately a five-fold molar excess was ligated to 10 ug of pJL6 DNA that had been cleaved with both HindIII and NdeI enzymes and purified over a NACS PREPAC minicolumn (Bethesda Research Laboratories) using the manufacturer's directions. The chimeric plasmidsynthetic heteroduplex DNA which was joined at the common HindIII site was purified from unligated material by chromatography on a NACS PREPAC minicolumn (Bethesda Research Laboratories). The purified chimeric DNA was then treated with 3.7 units of T4 DNA polymerase for 5 minutes at 37° C. in a 10 ul reaction mixture containing 33 mM Tris-acetate, pH 7.9, 66 mM potassium acetate, 10 mM magnesium acetate, 0.5 mM dithiothreitol, and 100 ug/ml BSA. The reaction was terminated by addition of Na3EDTA to 10 mM. The solution was extracted once with phenol:chloroform (1:1) and once with ether; residual traces of ether were removed in vacuo. Then the chimeric DNA was circularized by heating it to 65° C. and slowly cooling the reaction mixture to 4° C.

The resulting circular chimera contained single-stranded gaps on each side of the annealed region which were filled in with the Klenow fragment of E. coli DNA polymerase I. This was accomplished with 5 ug chimeric DNA in 50 ul of a solution containing 50 mM Tris-HCl, oH 7.8, 60 mM MgCl$_2$, 1 mM dATP, 1 mM dCTP, 1 mM dGTP, 1 mM TTP, 10 mM 2-mercaptoethanol, 50 ug/ml BSA, and 1 unit of the Klenow fragment of E. coli DNA polymerase I. This reaction mixture was incubated at room temperature for 15 minutes, then 10 ul of 10X ligation buffer (10X =0.66 M Tris-HCl, oH 7.6, 10 mM ATP, 10 mM spermidine, 0.1 M MgCl$_2$, 150 mM dithiothreitol, and 2 mg/ml BSA), 3 units of T4 DNA ligase and water (to 100 ul total reaction volume) were added. This reaction mixture was incubated at 16° C. for 3–4 h before being used directly to transform E. coli strain MH01 (100 ng DNA per transformation).

Colonies carrying the desired plasmid construct were identified by colony hybridization. Oligodeoxynucleotide F was radiolabeled using T4 polynucleotide kinase and [γ-$^{32}$P]ATP and was used as a probe in colony blots. Hybridization to lysed colonies immobilized on nitrocellulose filters occurred overnight at 37° C. in 37% formamide, 5X Denhardt's solution, 250 ug/ml yeast tRNA, 1.0 M NaCl, 0.1 M Tris-HCl, pH 8.0, 6 mM Na3EDTA and 0.1% SDS. Plasmids prepared from colonies hybridizing to the radiolabeled probe were checked for the presence of an ApaI restriction site by treatment with ApaI enzyme and analysis on agarose gels.

One plasmid that contained an ApaI site was subjected to plasmid DNA sequencing by the method disclosed in Chen and Seeburg, 1985, DNA, 4:165–170. A pBR322 HindIII site 16-mer orimer (New England Biolabs) that could be extended in a counterclockwise fashion relative to the conventional pBR322 physical mao was used in these DNA sequencing reactions. The sequencing results were confirmed and extended by the method disclosed in Guo and Wu, 1982, Nucleic Acids Res., 10:2065–2084. Briefly, the plasmid bearing an ApaI site was digested with EcoRv restriction enzyme, then subjected to limited digestion with *E. coli* exonuclease III. Repair synthesis in the presence of all four standard dideoxy-nucleotides (ddATP, ddCTP, ddGTP, and ddTTP) as well as dATP, dCTP, dGTP, and TTP was conducted using the Klenow fragment of *E. coli* DNA polymerase I The plasmid was then digested with AvaI restriction enzyme and the resultant DNA was analyzed by electrophoresis on polyacrylamide sequencing gels. Determination of the DNA sequence around the ApaI recognition site in this plasmid showed that DNA between the NdeI and HindIII cleavage sites on the coding strand in oJL6 had been replaced with the following sequence (coding strand): 5'- TATGGGGCCCTA - 3'. In addition, an A to G transition had occurred during the plasmid construction at a position 5' to the cII gene translational initiation codon, producing a base sequence in this region which reads:

5'-... TAAGGAAGTACTTACAT*ATG ....-3'

Figure 1:
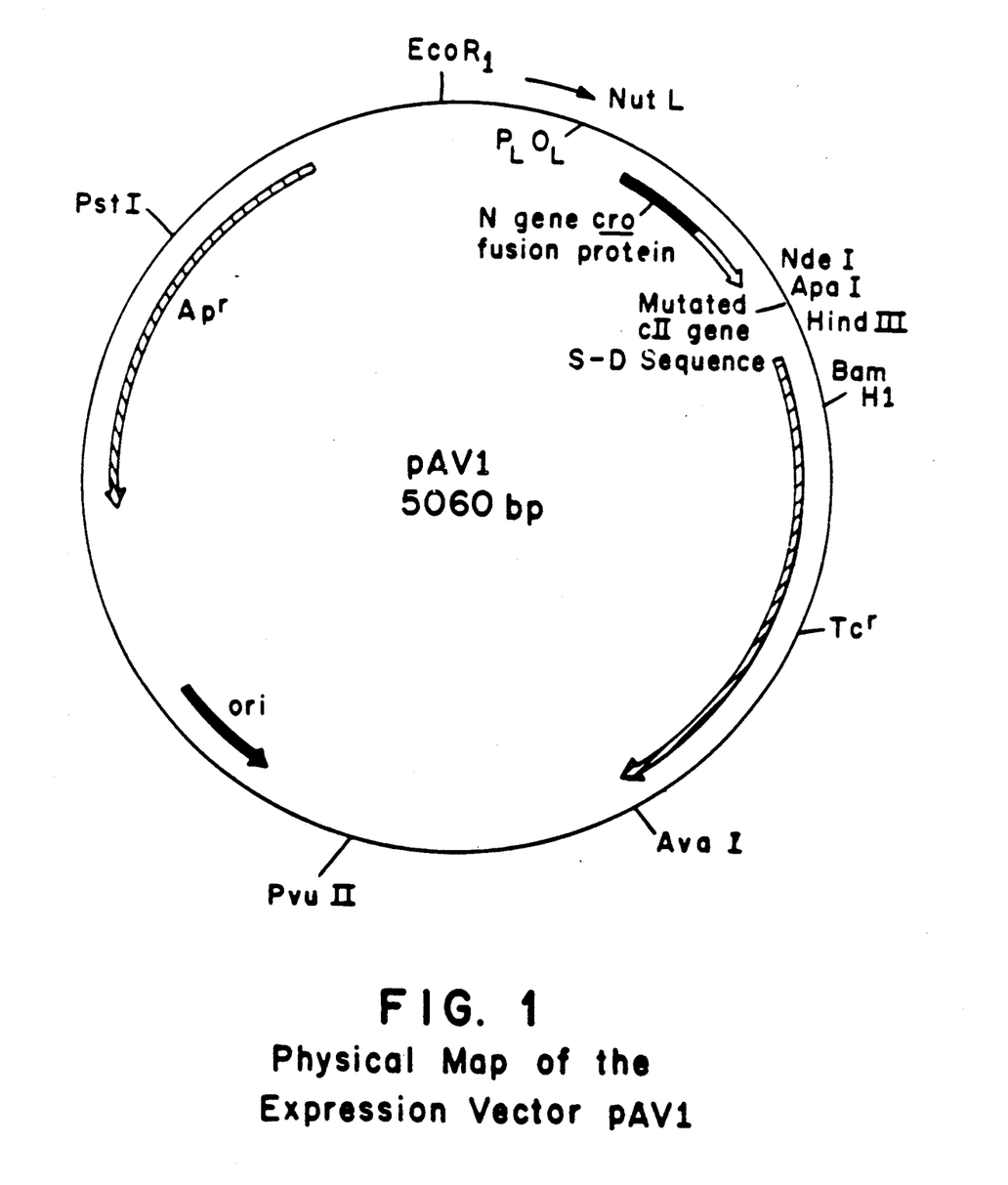
FIG. 1 is a physical map of the expression vector PAVl.

The starred base is the mutated base, while the underlined regions are respectively the Shine-Delgarno sequence and the translational initiation codon in this newly constructed plasmid. This plasmid was designated pAVl; a physical mao of pAVl is shown in the accompanying figure.

EXAMPLE 9

Preparation of a Synthetic Gene Without DNA Linkers For an Elastin Analogue

The following complementary and overlapping oligodeoxynucleotides were prepared as described in Example

5'-TTCCGGGTGTTGGTG-3'   F.

3'-CCACAACCACAAGGC-5'   G.

The final products were greater than 97% pure, determined as described in Example 1. Phosphate was added to the 5' ends of oligodeoxynucleotides F and G in separate reactions that contained 0.57 nmol oligodeoxynucleotide in 20 ul of the buffer described for the analogous reaction in Example 1 except that unlabeled ATP was added (1 mM). The kinased oligodeoxynucleotides were then combined and heated to 70° C. for 15 minutes to inactivate the kinase enzyme. A portion of each of the prepared oligodeoxynucleotides F and G was separately radiolabeled using T4 polynucleotide kinase and [γ−32P]ATP. Two pmol of each radiolabeled oligodeoxynucleotide was added to the reaction mixture containing the unlabeled oligodeoxynucleotides F and G, and the temperature of the mixture was allowed to decrease slowly from 70° C. to 1° C. overnight. By allowing aligonucleotides F and G to anneal under these conditions, the formation of the most stable heteroduplex is favored. In this case, one which contains 10 base pairs with a 5 base 5' overhang on each oligodeoxynucleotide strand is the favored heteroduplex. The 5' overhanging ends can further base pair with one another to generate, upon enzymatic ligation, a long synthetic DNA gene coding for an elastin analogue composed of repeats of the sequence Val-Pro-Gly-Val-Gly. After annealing of the oligodeoxynucleotides F and G, fresh ATP (63 uM) and T4 DNA ligase enzyme (5 units) were added to the reaction mixture. The temperature of the reaction mixture was then slowly increased to 14° C. over a 2 h period and incubation of the mixture was continued at 14° C. overnight. Large synthetic DNA genes were then obtained by size fractionating the enzymatic ligation products using chromatography on Sepharose 4B (Pharmacia). The relative size of synthetic gene DNAs in each fraction was determined as described in Example 1. Any DNA nicks and/or gaps were removed from 0.5 ug of synthetic gene DNA by *E. coli* DNA polymerase I as described in Example 1 except the final concentration of each of dATP, dCTP, dGTP and TTP was 0.33 mM. The DNA products were directly ligated to ClaI-digested and blunt-ended pJL6 plasmid DNA as described in Example 1. The ligation reaction was diluted to 200 ul in TE buffer and used directly to transform *E. coli* strain MH01 as described in Example 3.

Bacterial transformant colonies containing plasmids carrying synthetic gene inserts were identified and characterized by physical mapping using restriction enzymes as described in Example 3 for synthetic collagen analogue genes. Oligodeoxynucleotide F was used as a radiolabeled hybridization probe in these experiments. The hybridization temperature was 27° C. using this probe and buffer washes were conducted at 30+ C. rather than 55° C.

EXAMPLE 10

Preparation of ApaI Linkers and Attachment to a Collagen Analogue Gene to Form a Gene Cassette The following complementary and overlapping ol godeoxynucleotides were prepared and purified as described in Example 9:

5'-GGGCCCCCG-3'   H.

3'-GGCCCCGGG-5'   I.

The addition of phosphate to and the annealing of oligodeoxynucleotides H and I were as described in Example 9 except the solution in the annealing step was cooled to room temperature rather than 1° C. Proper annealing of oligodeoxynucleotides H and I to form ApaI linkers was followed by electrophoresis of samples on 20% polyacrylamide gels.

The following oligodeoxynucleotide was then chemically prepared and purified as described in Example 1:

5'-GGTCCGCCGGGTCCGCCG-3'   J.

The purified preparation of oligodeoxynucleotide J contained no detectable impurities, determined as described in Example 1. Oligodeoxynucleotide J is complementary to and overlaps with oligodeoxynucleotide B of Example 1. The addition of phosphate to and annealing and ligation of oligodeoxynucleotides B and J to form large synthetic genes was accomplished in substantially like manner to that described for oligodeoxynucleotides F and G of Example 9. Using those annealing conditions, the favored heteroduplex between oligodeoxynucleotides B and J is one that contains 15 base pairs with 3 base 3' overhanging ends on each oligodeoxynucleotide strand. The 3' overhanging ends can further base pair with one another to form, upon ligation, long synthetic collagen analogue genes coding for repeats of the amino acid sequence Gly-Pro-Pro. The synthetic DNA genes so formed were then size fractionated by chromatography on Sepharose 4B (Pharmacia) and the relative size of synthetic gene DNA in each fraction was assessed as described in Example 1. One factor which may ultimately limit the length of synthetic gene DNA attainable during the preceding step is the ligation of oligodeoxynucleotides lacking 5' phosphates at each growing end of these molecules. To insure that the large synthetic gene DNA does contain phosphate on its 5' ends, the kinase reaction was repeated as described before in several Examples. ApaI linkers (23 pmol) were attached to a portion of this material (about 0.23 omol) in the kinase reaction mixture after adjusting the ATP concentration to 2 mM and adding 4 units of T4 DNA ligase enzyme. After incubating the reaction mixture at 14° C. overnight, any nicks and/or gaps were removed by adding 37 ul 5X polymerase buffer (5X=250 mM Tris-HCl, pH 7.8, 45 mM MgCl$_2$, 50 mM 2-mercaptoethanol, and 250 ug/ml of BSA), dATP, dCTP, dGTP and TTP to 1 mM, and 7 units of E. coli DNA polymerase I in a total volume of 185 ul. This reaction mixture was incubated at 14° C. for 1 h, and then extracted once with phenol:chloroform (1:1). The DNA was then precipitated and digested with ApaI enzyme (up to 100 units) for as long as two days in reaction mixtures that contained 5 mM Tris-HCl, pH 7.4, 6 mM NaCl, 6 mM MgCl$_2$, 6 mM 2-mercaptoethanol, and 100 ug/ml of BSA. After extraction once with phenol:chloroform (1:1), the DNA products were passed over a Sepharose 4B (Pharmacia) column to remove digested ApaI linkers. The resulting synthetic collagen gene cassettes carrying ApaI linker ends were then ethanol precipitated after pooling the excluded fractions from the Sepharose 6B column.

EXAMPLE 11

Transformation of DC1138 with and Identification of Plasmids Bearing Collagen Analogue Genes With DNA Linkers (Gene Cassettes)

Collagen analogue gene cassettes carrying ApaI linker ends were ligated into oAVl DNA that had been digested with ApaI. Typical ligation reactions contained about 0.3 to 1.2 pmole collagen analogue gene cassettes and 0.03 to 0.12 pmole ApaI-digested plasmid vector in reaction volumes of 10-17 ul. Reaction buffer and other conditions were similar to those in previous Examples. The reactions were diluted to 1 ng total DNA per ul of solution using TE buffer as diluent and were then used to transform E. coli strain DC1138 as described in Example 3. Three to 10 ng total DNA were used on each transformation plate. Identification of transformant colonies containing plasmids carrying collagen analogue gene cassettes was as described in Example 3. In addition, restriction mapping with the enzymes EcoR1 and HindIII was used to give a rough estimate of the size of synthetic gene inserts in pAVl. After more accurate sizing of interesting synthetic gene inserts was completed using the restriction enzymes NdeI and HindIII, the size of the collagen analogue gene cassette was confirmed by digestion of the recombinant plasmid DNA with the enzymes BanII and/or Aoa I. Many transformants containing plasmids carrying collagen analogue gene cassettes were identified. Characterization of some of these showed that gene inserts identifiable as single gene cassettes in the bacterial clones analyzed ranged from about 170 to about 350 base pairs in length.

EXAMPLE 12

Identification of a Bacterial Clone Containing a Plasmid With Multiple Collagen Analogue Gene Cassettes Ligation, transformation, and identification of colonies containing plasmids carrying multiple collagen analogue gene cassettes were as described in Example 11. By using a ten to one molar excess of collagen analogue gene cassettes to plasmid expression vector DNA, the likelihood was increased in this Example that multiple cassettes will be incorporated into a single plasmid. One plasmid was identified as containing a synthetic gene insert of about 440 base pairs when digested with the restriction enzymes NdeI and HindIII. ApaI digestion of this plasmid (designated pAC95) yielded two collagen analogue gene cassettes, one about 200 base pairs and the other about 230 base pairs in length. The NdeI-HindIII synthetic gene cassette fragment was subcloned into the sequencing vector Bluescript M13+(Stratagene, San Diego, Calif.) and RNA transcripts of the synthetic gene cassette fragment were prepared. These RNA transcripts were then sequenced with avian myoblastosis reverse transcriptase enzyme and appropriate oligodeoxynucleotide primers according to the suppliers specifications. Sequence analysis of the NdeI-HindIII region of pAC95 which surrounds the two ApaI sites external to the insert DNA contained within pAC95 showed that the two gene cassettes were inserted in tandem within the ApaI sites of pAVl in the appropriate orientation with respect to the translation initiation signal sequence of the vector. Expression of the tandemly arranged gene cassettes in pAC95 should therefore produce the peptide Met-(Gly-Pro-Pro)48-Gly-pro.

What is claimed is:

1. A method of producing a gene cassette coding for polypeptides comprised of one or more repeating amino acid sequences, said method comprising the steps of
   (a) annealing at least one mixture of complementary but circularly permuted oligodeoxynucleotides which have phosphorylated 5' ends and which code for one or more repeating amino acid sequences, to form DNA$_1$ fragments, each having (i) an internal double stranded sequence of paired bases and (ii) a single-stranded sequence of unpaired bases of both ends of the double stranded internal sequence, said mixture being annealed by heating said mixture and thereafter cooling said heated mixture to allow formation of said DNA$_1$ fragments;
   (b) annealing a mixture of complementary but circularly permuted oligodeoxynucleotides which have phosphorylated 5' ends to form DNA$_2$ linker fragments, each having at least one restriction enzyme recognition site which does not occur within said DNA$_1$ fragments but occurs within the DNA of a plasmid vector, said DNA$_2$ linker fragments having (i) a single-stranded sequence of unpaired bases at both ends thereof which is complementary to a single-stranded sequence of a corresponding DNA$_1$ fragment and (ii) an internal double stranded sequence of paired bases, said linker DNA$_2$ fragments adapted to maintain the reading frame and to maintain the repeating amino acid sequence of the internal sequence of the DNA$_1$ fragments when said DNA₂ linker fragments and said DNA₁ fragments are attached enzymatically in tandem in said plasmid vector, said mixture of oligodeoxynucleotides being annealed by heating said mixture and thereafter cooling said heated mixture to allow formation of said DNA₂ fragments;

(c) combining all or a portion of said mixture of DNA₁ fragments and all or a portion of said mixture of DNA₂ linker fragments to form a combined mixture and further cooling said combined mixture to allow oligomerization, by annealing of complementary single-stranded sequences, of said DNA₂ linker fragments and of said DNA₁ fragments with themselves and with each other to form nicked DNA₃ fragments consisting of DNA₁ fragments interspersed DNA₂ linker fragments;

(d) treating said cooled combined mixture with an enzyme to covalently join adjacent oligodeoxynuxleotides in said nicked DNA₃ fragments to form DNA₄ fragments;

(e) treating said DNA₄ fragments with a restriction endonuclease to cleave said fragments at said restriction site to form gene cassettes which code for polypeptides having one or more repeating amino acid sequences.

2. A method according to claim 1 wherein in steps (a) and (b) each of said mixtures is cooled at a rate and to an extent such that the maximum amount of base pairing occurs between said oligodeoxynucleotides.

3. A method according to claim 1 wherein said DNA₂ linker fragments are selected such that they provide nonequivalents ends when attached to said DNA₁ fragments.

4. A method according to claim 1 wherein said DNA₁ fragments and said DNA₂ linker fragments are synthetic.

5. A method according to claim 1 which further comprises isolating said gene cassettes.

6. A method according to claim 1 wherein said linker DNAs are selected such that, when treated with an appropriate restriction enzyme capable of cutting at least one enzyme recognition site in said linker DNAs, they provide equivalent ends.

7. A method according to claim 1 wherein said linker DNAs are comprised of the oligodeoxynucleotides with sequences:

5'-GGGCCCCCG-3' and 5'-GGGCCCCGG-3'.

8. A method according to claim 1 wherein said linker DNAs are selected such that when treated with an appropriate restriction enzyme capable of cutting at least one enzyme recognition site in said linker DNAs they provide nonequivalent ends.

9. A method according to claim 8 wherein said linker DNAs are comprised of the oligodeoxynucleotides with sequences:

5'-GGGCCGCCAGGGCCGCCG-3' and

5'-CGGCCCTGGCGGCCCCGG-3'.

10. A method according to claim 1 wherein said gene cassettes code for repeats of the collagen analogue tripeptide sequence (Gly-Pro-Pro), or repeats of the elastin analogue pentapeptide sequence (Val-Pro-Gly-Val-Gly).

11. A process according to claim 1 which further comprises:

treating a plurality of one type of said cassettes with ligase to covalently join two or more adjacent gene cassettes so as to maintain the reading frame of the cassettes to form a multiple tandem gene cassette which codes for homopolypeptides having one or more repeating amino acid sequences, and having a molecular weight which is greater than the molecular weight of a polypeptide coded for by the single gene cassettes forming said multiple tandem gene cassette.

12. A method according to claim 11 which further comprises isolating said multiple tandem gene cassettes.

13. A method according to claim 11 wherein said multiple tandem gene cassettes code for a polypeptide homopolymer consisting of repeats of the collagen analogue tripeptide sequences (Gly-Pro-Pro) or repeats if the elastin analogue pentapeptide sequences (Val-Pro-Gly-Val-Gly).

14. A method of forming a recombinant plasmid comprising a replicable plasmid cloning vehicle, said method comprising the steps of:

(a) cleaving a plasmid cloning vehicle at a predetermined restriction endonuclease recognition site; and (b) enzymatically inserting one or more of the multiple tandem gene cassettes produced by the process of claim 11 at said site, such that said cassettes are under the control of a regulatable gene promoter sequence in said plasmid cloning vehicle whereby said inserted cassettes are expressible to form homopolypeptides when said recombinant plasmid is cloned in a suitable host microbial organism.

15. A process according to claim 1 which further comprises:

forming a mixture comprising two or more types of gene cassettes, at least one type of said cassette coding for a polypeptide having one or more repeats of amino acid sequences which are different from the amino acid sequences forming the repeats of the polypeptide coded for by at least one other type of gene cassette; and treating said mixture said ligase to covalently join two or more adjacent gene cassettes so as to maintain the reading frame of the individual cassettes to form a multiple tandem gene cassette which codes for a heteropolypeptide copolymer, said copolymer comprising one or more repeats of more than one type of amino acid sequence, and said copolymer having a molecular weight which is greater than the molecular weight of the polypeptides coded for by individual gene cassettes forming said multiple tandem gene cassette.

16. The method of claim 15 wherein said polypeptide copolymer comprises random or alternating repeats of two amino acid sequences.

17. A method according to claim 15, which further comprises isolating said formed multiple tandem gene cassettes.

18. A method according to claim 15, wherein said joined multiple tandem gene cassettes code for a polypeptide copolymer comprised of random or alternating repeats of two amino acid sequences, one of said sequences being the collagen analogue tripeptide sequence (Gly-Pro-Pro) and one of said sequences being the elastin analogue pentapeptide sequence (Val-Pro-Gly-Val-Gly).

* * * * *